United States Patent
Chen et al.

(10) Patent No.: US 7,652,168 B2
(45) Date of Patent: *Jan. 26, 2010

(54) SYNTHESIS OF TAXOL ENHANCERS

(75) Inventors: Shoujun Chen, Billerica, MA (US);
Lijun Sun, Harvard, MA (US);
Zhi-Qiang Xia, Dedham, MA (US);
Keizo Kova, Brookline, MA (US);
Mitsunori Ono, Lexington, MA (US)

(73) Assignee: Synta Pharmaceuticals Corp.,
Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/231,217

(22) Filed: Aug. 29, 2008

(65) Prior Publication Data

US 2009/0005594 A1    Jan. 1, 2009

Related U.S. Application Data

(63) Continuation of application No. 11/440,429, filed on May 24, 2006, now Pat. No. 7,435,843, which is a continuation of application No. 10/807,919, filed on Mar. 24, 2004, now Pat. No. 7,074,952, which is a continuation of application No. 10/193,076, filed on Jul. 10, 2002, now Pat. No. 6,825,235.

(60) Provisional application No. 60/304,318, filed on Jul. 10, 2001.

(51) Int. Cl.
*C07C 327/56* (2006.01)

(52) U.S. Cl. ...................................... 564/74
(58) Field of Classification Search ............... None
See application file for complete search history.

(56) References Cited

U.S. PATENT DOCUMENTS

| 4,012,360 | A | 3/1977 | Schwarzenbach et al. |
| 4,822,777 | A | 4/1989 | Abra |
| 4,826,866 | A | 5/1989 | Taylor et al. |
| 5,300,278 | A | 4/1994 | Pasqualini et al. |
| 5,498,421 | A | 3/1996 | Grinstaff et al. |
| 5,560,933 | A | 10/1996 | Soon Shiong et al. |
| 5,665,382 | A | 9/1997 | Grinstaff et al. |
| 5,739,686 | A | 4/1998 | Naughton et al. |
| 5,753,200 | A | 5/1998 | Zolotoochin et al. |
| 5,840,746 | A | 11/1998 | Ducharme |
| 5,843,400 | A | 12/1998 | Fujibayashi et al. |
| 5,916,596 | A | 6/1999 | Desai et al. |
| 6,013,836 | A | 1/2000 | Hsu et al. |
| 6,096,331 | A | 8/2000 | DeSai et al. |
| 6,172,108 | B1 | 1/2001 | Vega et al. |
| 6,172,188 | B1 | 1/2001 | Thastrup et al. |
| 6,214,863 | B1 | 4/2001 | Bissery et al. |
| 6,235,787 | B1 | 5/2001 | Broadhurst et al. |
| 6,365,745 | B1 | 4/2002 | Matsui et al. |
| 6,399,659 | B2 | 6/2002 | Usui et al. |
| 6,435,787 | B1 | 8/2002 | John |
| 6,455,515 | B2 | 9/2002 | Gypser et al. |
| 6,506,405 | B1 | 1/2003 | DeSai et al. |
| 6,537,579 | B1 | 3/2003 | DeSai et al. |
| 6,656,971 | B2 | 12/2003 | Wu et al. |
| 6,703,426 | B1 | 3/2004 | Miles et al. |

(Continued)

FOREIGN PATENT DOCUMENTS

AU    2006-228035 A1    10/2006

(Continued)

OTHER PUBLICATIONS

"Activating Agents and Protecting Groups," *Handbook of Reagents for Organic Synthesis*, pp. 133-135.

(Continued)

*Primary Examiner*—Fiona T Powers
(74) *Attorney, Agent, or Firm*—Foley & Lardner LLP; Steven G. Davis

(57) ABSTRACT

Disclosed is a method of preparing a thiohydrazide product compound from a hydrazide starting compound. The hydrazide starting compound is represented by Structural Formula (I):

$$\underset{R_2}{\overset{R_1}{\diagdown}}\underset{\underset{R_{10}}{|}}{N}-N\diagup^{R_5} \quad \text{with C=O} \tag{I}$$

The thiohydrazide product compound is represented by Structural Formula (II):

$$\underset{R_2}{\overset{R_1}{\diagdown}}\underset{\underset{R_{10}}{|}}{N}-N\diagup^{R_5} \quad \text{with C=S} \tag{II}$$

In Structural Formulas (I)-(II), $R_1$ and $R_2$ are independently an aliphatic group, a substituted aliphatic group, an aryl group or a substituted aryl group, or $R_1$ and $R_2$ taken together with the carbon and nitrogen atoms to which they are bonded, form a non-aromatic heterocyclic ring optionally fused to an aromatic ring. When $R_2$ is an aryl group or a substituted aryl group, then $R_5$ is a hydrazine protecting group; and when $R_2$ is an aliphatic or substituted aliphatic group, then $R_5$ is —H or a hydrazine protecting group. $R_{10}$ is —H or a substituted or unsubstituted alkyl group. The method comprising the step of reacting the starting compound with a thionylating reagent.

8 Claims, No Drawings

U.S. PATENT DOCUMENTS

| | | |
|---|---|---|
| 6,749,868 B1 | 6/2004 | DeSai et al. |
| 6,753,006 B1 | 6/2004 | DeSai et al. |
| 6,762,204 B2 | 7/2004 | Koya et al. |
| 6,800,660 B2 | 10/2004 | Koya et al. |
| 6,809,119 B2 | 10/2004 | Hu et al. |
| 6,825,235 B2 * | 11/2004 | Chen et al. .......... 514/599 |
| 6,897,335 B2 | 5/2005 | Okabe et al. |
| 6,924,312 B2 | 8/2005 | Koya et al. |
| 7,001,923 B2 | 2/2006 | Koya et al. |
| 7,037,940 B2 | 5/2006 | Koya et al. |
| 7,074,952 B2 | 7/2006 | Chen et al. |
| 7,250,432 B2 | 7/2007 | Kwon et al. |
| 7,345,094 B2 | 3/2008 | Koya et al. |
| 7,368,473 B2 | 5/2008 | Koya et al. |
| 7,385,084 B2 | 6/2008 | Koya et al. |
| 7,435,843 B2 | 10/2008 | Chen et al. |
| 2002/0198160 A1 | 12/2002 | Everitt et al. |
| 2004/0022869 A1 | 2/2004 | Chen et al. |
| 2004/0225016 A1 | 11/2004 | Koya et al. |
| 2004/0235813 A1 | 11/2004 | Wanker et al. |
| 2005/0154039 A1 | 7/2005 | Glacera Contour |
| 2006/0142386 A1 | 6/2006 | Barsoum |
| 2006/0142393 A1 | 6/2006 | Sherman et al. |
| 2006/0167106 A1 | 7/2006 | Zhang et al. |
| 2006/0270873 A1 | 11/2006 | Chen et al. |
| 2007/0088057 A1 | 4/2007 | Lunsmann et al. |
| 2008/0089950 A1 | 4/2008 | Chen et al. |
| 2008/0118562 A1 | 5/2008 | Koya |
| 2008/0119440 A1 | 5/2008 | Koya |
| 2008/0146842 A1 | 6/2008 | Chen et al. |
| 2008/0176828 A1 | 7/2008 | Williams et al. |
| 2008/0214655 A1 | 9/2008 | Koya et al. |
| 2008/0226588 A1 | 9/2008 | McLeod |
| 2008/0242702 A1 | 10/2008 | Koya et al. |
| 2008/0269340 A1 | 10/2008 | Koya et al. |
| 2009/0005594 A1 | 1/2009 | Chen et al. |
| 2009/0023736 A1 | 1/2009 | Koya et al. |
| 2009/0042991 A1 | 2/2009 | Barsoum |
| 2009/0093538 A1 | 4/2009 | Bertin et al. |
| 2009/0137682 A1 | 5/2009 | Dahl |

FOREIGN PATENT DOCUMENTS

| | | |
|---|---|---|
| CH | 482 394 A | 12/1969 |
| DE | 2 037 257 A1 | 2/1972 |
| EP | 1 454 628 A2 | 9/2004 |
| EP | 1 493 445 A1 | 1/2005 |
| EP | 1 406 869 B1 | 9/2006 |
| EP | 1 731 148 A1 | 12/2006 |
| EP | 1 845 083 A2 | 10/2007 |
| FR | 2 097 737 | 4/1972 |
| GB | 1 272 920 | 5/1972 |
| JP | 50-91056 | 7/1975 |
| JP | 63-267752 | 11/1988 |
| JP | 07-165693 | 6/1995 |
| JP | 10-501215 | 2/1998 |
| WO | WO 94/10995 A1 | 5/1994 |
| WO | WO 99/34796 A1 | 7/1999 |
| WO | WO 03/006428 A1 | 1/2003 |
| WO | WO 03/006429 A1 | 1/2003 |
| WO | WO 03/006430 A1 | 1/2003 |
| WO | WO 03/047524 A2 | 6/2003 |
| WO | WO 2004/064826 A1 | 8/2004 |
| WO | WO 2004/072051 A1 | 8/2004 |
| WO | WO 2005/028475 A2 | 3/2005 |
| WO | WO 2005/097758 A1 | 10/2005 |
| WO | WO 2006/009940 A1 | 1/2006 |
| WO | WO 2006/033913 A2 | 3/2006 |
| WO | WO 2006/055747 A2 | 5/2006 |
| WO | WO 2006/062732 A2 | 6/2006 |
| WO | WO 2006/089177 A2 | 8/2006 |
| WO | WO 2006/113493 A2 | 10/2006 |
| WO | WO 2006/113572 A1 | 10/2006 |
| WO | WO 2006/113695 A1 | 10/2006 |
| WO | WO 2006/124736 A2 | 11/2006 |
| WO | WO 2007/021881 A1 | 2/2007 |
| WO | WO 2008/024298 A1 | 2/2008 |
| WO | WO 2008/024299 A2 | 2/2008 |
| WO | WO 2008/024301 A2 | 2/2008 |
| WO | WO 2008/024302 A2 | 2/2008 |
| WO | WO 2008/024303 A2 | 2/2008 |
| WO | WO 2008/024305 A2 | 2/2008 |
| WO | WO 2008/027445 A2 | 3/2008 |
| WO | WO 2008/033300 A2 | 3/2008 |
| WO | WO 2008/033449 A2 | 3/2008 |
| WO | WO 2008/033494 A2 | 3/2008 |
| WO | WO 2008/082579 A1 | 7/2008 |
| WO | WO 2008/136976 A2 | 11/2008 |
| WO | WO 2009/020631 A2 | 2/2009 |
| WO | WO 2009/064374 A2 | 5/2009 |
| WO | WO 2009/073147 * | 6/2009 |
| WO | WO 2009/073147 A2 | 6/2009 |
| WO | WO 2009/073148 A2 | 6/2009 |

OTHER PUBLICATIONS

Badawy, M.A., "Synthesis and Reactions of 1,2,4-Triazino-1,2,4-Triazines," *Sulfur Letters* 11(1+2):21-28 (1990).

Baker, W. et al., "663: 1 : 4-*Diaryl*-1: 4-*dihydro*-1 : 2 : 4 : 5-*tetrazines and Derived Substances*," *Journal of The Chemical Society*, 3389-3394 (1950).

Barta-Szalai, G. et al., "Electron Deficient Heteroaromatic Ammonioamidates. XVII. N-(3-Quinazolinio)amidates. VI. The Photochemistry of N-(3-Quinazolinio)amidates in the Presence of ÿ-Toluenethiol," *Acta Chemica Scandinavica B* 33:79-85 (1979).

Branch, C.L. et al., "Synthesis of 6-Hydroxy-2-Methyl-3-Thioxo-2H-1,2,4-Triazin-5-one," *Synthetic Communications* 26(11):2075-2084 (1996).

Cava, M.P. et al., "Thionation Reactions of Lawesson's Reagents," *Tetrahedron*, 14(22): 5061-5087 (1985).

El-Barbary, A.A. et al., "Studies in Organophosphorus Compounds," *Tetrahedron*, 36: 3309-3315 (1980).

Greene, T.W. et al., "Protection For The Amino Group," *Protective Groups in Organic Synthesis*, Third Edition, 7, pp. 494-653.

Greene, T.W. et al., "Protection For The Carboxyl Group," *Protective Groups in Organic Synthesis*, Third Edition, 5, pp. 369-453.

Heindel, N.D. et al., "Thiohydrazides and Acetylene Esters, A New Route to 1,3,4-Thiadiazoles," *Journal of Heterocyclic Chemistry*, 17(1): 191-193 (1980).

Henderson, N.D. et al., "Synthesis of new bifunctional compounds which selectively alkylate guanines in DNA," *Anti-Cancer Drug Design*, 13:749-768 (1998).

Jensen, K.A. et al., "Thiohydrazides and Thiohydrazones: A New Class of Antibacterial Substances," *Acta Chemica Scandinavica*, 6(Pt. II): 957-958 (1952).

Metzner, P. et al., "Sulfur Reagents in Organic Synthesis," *Best Synthetic Methods*, pp. 30-185.

Mohamed, M.M. et al., "Synthesis & Some Reactions of 2-(α/β-Naphthyl)-3,1-benzoxazin-4(H)-ones 3-Amino-2-(ÿ-naphthyl)quinazolin-4(3H)-one," *Indian Journal of Chemistry* 25B(2):207-211 (1986).

Molina, P. et al., "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1* s 5:1159-1166 (1991).

Molina, P. et al., "Preparation of a Novel Type of Ligands Incorporating Two or Three 1,3,4-Thiadiazole Units," *Heterocycles* 36(6):1263-1278 (1993).

Przheval, N.M. et al., "A New General Synthesis of Bistetrafluoroborates of 2,3,4,5-Tetrasubstituted 1,3,4-Thiadiazoliums," *Synthesis* 5:463-464 (1993).

Rupp, W., "5-Amino-1,3,4-Thiadiazole Compounds," CA76:126992 (1972).
Sato, T. et al., "Studies in Organic Sulfur Compounds. I. Thioformyl Phenylhydrazide," *Bulletin of the Chemical Society of Japan*, 27(9): 624-627 (1954).
Schwarz, J. and Just, H., "Virustatic Thiosemicarbazides," CA77:48081 (1972).
Tsuji, T. et al., "Synthesis and Reactions of N-Aminothiouracils and Thiadiazolo [3,2-ÿ] pyrimidinones," *Chem. Pharm. Bull.* 26(9):2765-2767 (1978).
Ueda, H. and Ohta, M., "Studies on Sulfur-Containing Heterocyclic Compounds," *Nippon Kagaku Zasshi*, 80:571-574 (1959).
Walter, W. et al., "Chapter 9: The Chemistry of the Thiohydrazide Group," *The Chemistry of Amides* (Ed. J. Zabicky), (London: Interscience Publishers), pp. 477-514 (1970).
"Remarks" paper as submitted by Applicant's Attorney on Oct. 24, 2002 for U.S. Appl. No. 10/193,075.
"The Merck Manual," Chapter 14: Principles of Cancer Therapy, 1999 Merck Research Laboratories, pp. 987-995 (1999), XP002477370.
Abuchowski, A. et al., "Alteration of Immunological Properties of Bovine Serum Albumin by Covalent Attachment of Polyethylene Glycol," The *Journal of Biological Chemistry* 252(11):3578-3581 (1977).
Al-Talib, M. et al., "Diacyl Acid Dihydrazides," *Magnetic Resonance in Chemistry*, 28: 1072-1078 (1990).
Asahi Chemical Ind. K.K. Abstract of Japanese Patent No. 50-91056, Accession No. 47521Y/27 (1975).
Ashburner, M. and Bonner, J.J., "The Induction of Gene Activity in *Drosophila* by Heat Shock," *Cell*, 17: 241-254 (1979).
Atherton, F.R. et al., "Synthesis of 3(*S*)-Acylamino-1-[(Phenyl)(1H-Tetrazol-5-YL)Amino]-2-Azetidinones," *Tetrahedron*, 39(15): 2599-2608 (1983).
Auluck, P.K. et al., "Chaperone Suppression of α-Synuclein Toxicity in a *Drosophila* Model for Parkinson's Disease," *Science*, 295: 865-868 (2002).
Bahceci et al., "Reactions of amidines with some carboxylic acid hydrazides," Indian Journal of Chemistry Section B, vol. 44B, 2005, pp. 568-572, XP009083365, p. 569, Scheme 1.
Chuyguk, V.A. and Nemazanyj A.G., "Mesoionic Methine Dyes from Biquaternary Salts of Dihetarylmethanes—1,3,4-Oxa(thia)diazoles and 1,2,4-Triazoles Derivatives," *Ukr. Khim. Zhurn.* 48:520 (1984). Translation submitted in U.S. Appl. No. 10/193,075, filed Jul. 10, 2002.
Clathrate: Lewis, Hawley's Condensed Chemical Dictionary, 14th Edition, 1997, Van Nostrand Reinhold.
Craig, E.A., "The Heat Shock," *Crit. Rev. Biochem.*, 18(3): 239-280 (1985).
Daniels, G. et al., "A simple method to cure established tumors by inflammatory killing of normal cells," Nature Biotechnoloyg, Sep. 2004, 22(9), 1125-1132 (Epub Aug. 1, 2004).
Doi, Y. et al., "Effect of HSP70 Induced by Warm Ischemia to the Liver on Liver Function after Partial Hepatectomy," *Hepato-Gastroenterology*, 48: 533-540 (2001).
Dunn, S.E. et al., "Polystyrene-Poly (Ethylene Glycol) (PS-PEG2000) Particles as Model Systems for Site Specific Drug Delivery. 2. The Effect of PEG Surface Density on the in Vitro Cell Initeraction and in Vivo Biodistribution," *Pharmaceutical Research* 11(7):1016-1022 (1994).
Dvorak, H.F. et al., "Identification and Characterization of the Blood Vessels of Solid Tumors That Are Leaky to Circulating Macromolecules," *American Journal of Pathology* 133(1):95-109 (1988).
Balkwill, F. et al., "Inflammation and Cancer: Back to Virchow?" *The Lancet*, 357: 539-545 (Feb. 2001).
Gabizon, A.A., "Selective Tumor Localization and Improved Therapeutic Index of Anthracyclines Encapsulated in Long-Circulating Liposomes," *Cancer Research* 52:891-896 (1992).
Gao, Y. et al., "Protein Kinase C-dependent Activation of P44/42 Mitogen-activated Protein Kinase and Heat Shock Protein 70 in Signal Transduction During Hepatocyte Ischemic Preconditioning," *World J. Gastroenterol.*, 10(7): 1019-1027 (2004).
Garloch, K., "Experimental Treatment Gives a Cancer Patient Hope," *The Charlotte Observer* [online], Apr. 25, 2005 [retrieved on May 23, 2008]. Retrieved from the Internet URL: http://www.ericandfran.com/charlotte_observer_april_25.htm.
Gavezzotti, "Are crystal structures predictable?," Accounts of Chemical Research, 27:309-314, 1994.
Gehrmann, M., "Drug Evaluation: STA-4783—Enhancing Taxane Efficacy by Induction of Hsp70," *Current Opinion in Investigational Drugs*, 7(6): 574-580 (Jun. 2006), XP008087326.
Georgopoulos, C. and Welch, W.J., "Role of the Major Heat Shock Proteins as Molecular Chaperones," *Annu. Rev. Cell Biol.*, 9: 601-634 (1993).
Golub et al., "Molecular Classification of Cancer: Class Discovery and Class Prediction by Gene Expression Monitoring," *Science*, 286, 1999, pp. 531-537.
Goodman & Gilman's, The Pharmacological Basis of Therapeutics, Ninth Edition, (1996), Section X, Calabresi et al., pp. 1225-1232.
Barclay, J.W. and Roberson, R.M., "Role for Calcium in Heat Shock-Mediated Synaptic Thermoprotection in *Drosophila* Larvae," *J. Neurobiol.*, 56(4): 360-371 (2003).
Barrett, William G. and McKay, Donald, "Decomposition and Cycloaddition Reactions of Some Bis(azodicarbonyl) Compounds," *Journal of Chem. Soc.*, (4): 1046-1052 (1975).
Gref, R. et al., "Biodegradable Long-Circulating Polymeric Nanospheres," *Science* 263:1600-1603 (1994).
Gura et al., "Systems for Identifying New Drugs are Often Faulty," *Science*, 1997, 278: 1041-1042.
Gurney, M.E. et al., "Motor Neuron Degeneration in Mice That Express a Human Cu,Zn Superoxide Dismutase Mutation," *Science*, 264: 1772-1775 (1994).
Barry, V.C. et al., "Anticancer Agents-III. Synthesis and Anticancer Activity of Some Bis-Thiosemicarbazones and Thiosemicarbazides," *Proc. R.I.A.*, 65: 309-324 (1967).
Beck, F-X. et al., "Molecular Chaperones in the Kidney: Distribution, Putative Roles, and Regulation," *Am. J. Physiol. Renal. Physiol.*, 279: F203-F215 (2000).
Hiratsuka, M. et al., "Heat Shock Pretreatment Protects Pulmonary Isografts from Subsequent Ischemia-reperfusion Injury," *J. Heart Lung Transplant*, 17(12): 1238-1246 (1998).
Holcomb, L. et al., "Accelerated Alzheimer-Type phenotype in transgenic mice carrying both mutant *amyloid precursor protein* and *presenilin 1* transgenes," *Nature Medicine*, 4(1): 97-100 (1998).
Honshu Paper Mfg. Co. Ltd, Abstract of Japanese Patent No. 182050, published Feb. 13, 1996.
Howland, D.S. et al., "Focal Loss of the Glutamate Transporter Eaat2 in a Transgenetic Rat Model of Sod1 Mutant-mediated Amyotrophic Lateral Sclerosis (ALS)," *Proc. Nat. Acad. Sci. USA*, 99(3): 1604-1609 (2002).
Ichihara et al., "Roles of oxidative stress and Akt signaling in doxorubicin cardiotoxicity," Biochemical and Biophysical Research Communications, Academic Press Inc., Orlando, FL, US, vol. 359, No. 1, Jun. 2, 2007, pp. 27-33, XP022103137, ISSN: 0006-291X.
Inclusion complex: Lewis, Hawley's Condensed Chemical Dictionary, 14th Edition, 1997, Van Nostrand Reinhold.
Ishii, Y. et al., "Retinal Ganglion Cell Protection with Geranylgeranylacetone, a Heat Shock Protein Inducer, in a Rat Glaucoma Model," *Invest. Opthalmol. Vis. Sci.*, 44(5): 1982-1992 (2003).
Jacquier-Sarlin, M.R. et al., "Protective Effects of hsp70 in Inflammation," *Experientia*, 50(11-12): 1031-1038 (Nov. 1994).
Beillerot et al., "Synthesis and protective effects of coumarin derivatives against oxidative stress induced by doxorubicin," Bioorganic & Medicinal Chemistry Letters, Oxford, GB, vol. 18, No. 3, Dec. 27, 2007, pp. 1102-1105, XP022475694, ISSN: 0960-894X.
Johnson, A.D. et al., "Differential Distribution of 70-kD Heat Shock Protein Atherosclerosis," *Arterio Thromb Vasc Biol*, 15(1): 27-36 (1995).
Kandror, O. and Goldberg, A.L., "Trigger Factor is Induced Upon Cold Shock and Enhances Viability of *Escherichia coli* at Low Temperatures," *Proc Natl Acad Sci USA*, 94(10): 4978-4981 (1997).
Kelly, S. and Yenari, M.A., "Neuroprotection: Heat Shock Proteins," *Curr Res Med Opin*, 18(Suppl. 2): s55-s60 (2002).
Keswani et al., "FK506 Is Neuroprotective in a Model of Antiretroviral Toxic Neuropathy," *Annals Neurology*, 53(1): 57-64 (2003).

Kiang, J.G. and Tsokos, G.C., "Heat Shock Protein 70 kDA: Molecular Biology, Biochemistry, and Physiology," *Pharmacol Ther*, 80(2): 183-201 (1998).

Klettner, A. and Herdegen, T., "The Immunophilin-Ligands FK506 and V-10,367 Mediate Neuroprotection by the Heat Shock Response," *Br J Pharmacol*, 138(5): 1004-1012 (2003).

Klettner, A., "The Induction of Heat Shock Proteins as a Potential Strategy to Treat Neurodegenerative Disorders," *Drug News Perspect*, 17(5): 299-306 (2004).

Klibanov, A. et al., "Amphipathic Polyethyleneglycols Effectively Prolong the Circulation Time of Liposomes," *FEBS* 268(1):235-237 (1990).

Kruse, L.I. et al., "Some Benzyl-Substituted Imidazoles, Triazoles, Terazoles, Pyridinethiones, and Structural Relatives as Multisubstrate Inhibitors of Dopamine β-Hydroxylase. 4.[1] Structure-Activity Relationships at the Copper Binding Site," *J. Med. Chem.*, 33: 781-789 (1990).

Langston, J.W. et al., "Selective Nigral Toxicity After Systemic Administration of 1-Methyl-4Phenyl-1,2,5,6-Tetrahydropyrine (MPTP) in the Squirrel Monkey," *Brain Res*, 292: 390-394 (1984).

Lee, J.E. et al., "Differential Neuroprotection From Human Heat Shock Protein 70 Overexpression in in Vitro and in Vivo Models of Ischemia and Ischemia-Like Conditions," *Exp Neurol*, 170(1): 129-139 (2001).

Lepore, D.A. et al., "Role of Priming Stresses and Hsp70 in Protection From Ischemia-Reperfusion Injury in Cardiac and Skeletal Muscle," *Cell Stress & Chaperones*, 6(2): 93-96 (2001).

Lindquist, S., "The Heat-Shock Response," *Ann Rev Biochem*, 55: 1151-1191 (1986).

Longa, E.Z. et al., "Reversible Middle Cerebral Artery Occlusion Without Craniectomy in Rats," *Stroke*, 20(1): 84-91 (1989).

Malberg, J.E. and Seiden, L.S., Poster "MDMA Administration Induces Expression of HSP70 in the Rat Brain." Society for Neuroscience Annual Meeting, New Orleans, LA, Oct. 25-30, 1997.

Mangiarini, L. et al. , "Exon 1 of the HD Gene With an Expanded CAG Repeat is Sufficient to Cause a Progressive Neurological Phenotype in Transgenic Mice," *Cell*, 87: 493-506 (1996).

Marber, M.S. et al., "Overexpression of the Rat Iducible 70-kD Heat Stree Protein in a Transgenic Mouse Increases the Resistance of the Heart to Ischemic Injury," *J Clin Invest*, 95: 1446-1456 (1995).

McCarthy, A.R. et al., "Cyclic Meso-ionic Compounds. Part IX.[1] Synthesis, Spectroscopic Properties, and Chemistry of 1,3,4-Thiadiazolium-2-olates and 1,3,4-Oxadiazolium-2-thiolates[2]," *J.C.S. Perkin I*, 627-632 (1974).

Merlin, J.-L. et al., "In vitro Comparative Evaluation of Trastuzumab (Herceptin®) Combined with Paclitaxel (Taxol®) or Docetaxel (Taxotere®) in HER2-Expressing Human Breast Cancer Cell Lines," Annals of Oncology, vol. 13: 1743-1748 (2002).

Bellmann, K. et al., "Heat Shock Induces Resistance in Rat Pancreatic Islet Cells against Nitric Oxide, Oxygen Radicals and Streptozotocin Toxicity In Vitro," *J. Clin. Invest.*, 95(6): 2840-2845 (1995).

Milas et al., "Chemoradiotherapy: emerging treatment improvement strategies," published online Dec. 6, 2003 in Wiley InterScience (www.interscience.wiley.com).

Minowada, G. and Welch, W.J., "Clinical Implications of the Stress Response," *J Clin Invest*, 95: 3-12 (1995).

Mitsui Toatsu Chem. Inc., Abstract of Japanese Patent No. 308024, published Dec. 25, 1986. From Derwent Publications Ltd.

Bräuniger, H., "Hydrazide und Hydrazidderivate von Dicarbonsäuren," Pharmaceutical-Chemical Institute of University of Rostock, Supplied by the "British Library," *Pharmazie*, 25(5-6): 279-283 (1970).

Brittain et al., in *Polymorphism in Pharmaceutical Solids*, (NY: M. Dekker), vol. 95, pp. 348-361 (1999).

Calderwood, S. et al., "Extracellular heat shock proteins in cell signaling and immunity," Annals of the New York Academy of Sciences, Oct. 2007, 1113, 28-39.

Morimoto et al., In: The Biology of Heat Shock Proteins and Molecular Chaperone. (NY: Cold Spring Harbor Laboratory Press) pp. 417-455 (1994).

Mosser, D.D. et al., "The Chaperone Function of hsp70 Is Required for Protecti Induced Apoptosis," *Mol Cell Biol*, 20(19): 7146-7159 (2000).

O'Callaghan, C.N., "Anticancer Agents-X. Cyclisation of 1-Acyl-4-Alkylthiosemicarbazide Derivatives to 1,2,4-Triazoline-3-Thiones in the Presence of Hydrazine," *Proc. R.I.A.*, 74: 455-461 (1974).

Papahadjopoulos, D. et al., "Sterically Stabilized Liposomes: Improvements in Pharmacokinetics and Antitumor Therapeutic Efficacy," *Proc. Natl. Acad. Sci. USA* 88:11460-11464 (1991).

Patani et al., "Bioisosterism: A Rational Approach in Drug Design," Chem. Rev., 96: 3147-3176 (1996), esp. p. 3152.

Notification of Transmittal of the International Preliminary Examination Report for International Application No. PCT/US 02/21716, mailed Sep. 19, 2003.

Notification of Transmittal of the International Search Report or the Declaration for International Application No. PCT/US 02/21716, mailed Nov. 15, 2002.

Notification of Transmittal of the Written Opinion of the International Searching Authority for International Application No. PCT/US 02/21716, mailed Feb. 20, 2003.

Plumier, J.-C. L. et al., "Transgenic Mice Expressing the Human Heat Shock Protein 70 Have I proved Post-Ischemic Myocardial Recovery," *J Clin Invest*, 95: 1854-1860 (1995).

Cancer, Wikipedia, http://en.wikipedia.org/wiki/Cancer (1 of 40) Aug. 2, 2008 (all pages).

Radford, N.B. et al., "Cardioprotective Effects of 70-kDa Heat Shock Proteiin in Transgenic Mice," *Proc Natl Acad Sci USA*, 93(6): 2339-2342 (1996).

Rao et al., "Combination of Paclitaxel and Carboplatin as Second-Line Therapy for Patients with Metastatic Melanoma," *Cancer*, vol. 106, No. 2: 375-382 (2006).

Renshaw, G.M.C. et al., "Oxygen Sensors and Energy Sensors Act Synergistically to Achieve a Graded Alteration in Gene Expression: Consequences for Assessing the Level of Neuroprotection in Response to Stressors," *Front Biosci*, 9: 110-116 (2004).

Carmel, J.B. et al., "Mediators of Ischemic Preconditioning Identified by Microarray Analysis of Rat Spinal Cord," *Exp. Neurol.*, 185: 81-96 (2004).

Sanchez et al., "New naphthylcombretastatins. Modifications on the ethylene bridge," Bioorganic and Medicinal Chemistry, vol. 13, No. 6, Mar. 2005, pp. 2097-2107, XP002470852, ISSN: 0968-0896.

Sato, K. et al., "HSP70 is Essential to the Neuroprotective Effect of Heat-Shock," *Brain Res*, 740(1-2): 117-123 (1996).

Carter, R. J. et al., "Characterization of Progressive Motor Deficits in Mice Transgenic for the Human Huntington's Disease Mutation," *J. Neuroscience*, 19(8): 3248-3257 (1999).

Sauer, H. and Oertel, W.H., "Progressive Degeneration of Nigrostriatal Dopamine Neurons Following Instrastriatal Terminal Lesions with 6-Hydroxydopamine: A Combined Retrograde Tracing and Immunocytochemical Study in the Rat," *Neuroscience*, 59(2): 401-415 (1994).

Sausville et al., "Contributions to Human Tumor Xenografts to Anticancer Drug Development," *Cancer Research*, 2006, vol. 66, pp. 3351-3354.

Savage, E. et al., Living with Melanoma, [online], [retrieved on Aug. 9, 2006]. Retrieved from the Internet URL: http://ericandfran.com/melanona.htm.

Schroeter, G. et al., "Über methionsäure und deren verwendung zu synthesen," Instit der Kgl. Tierärztlichen Hochschule Berlin, Oct. 26, 1918.

Chen, H-C. et al., Induction of Heat Shock Protein 70 Protects Mesangial Cells Against Oxidative Injury, *Kidney Int.*, 56: 1270-1273 (1999).

Shin, K.D. et al., "Blocking tumor cell migration and invasion with biphenyl isoxazole derivative KRIBB3, a synthetic molecule that inhibits Hsp27 phosphorylation" Journal of Biological Chemistry, American Society of Biolochemical Biologists, Birmingham, US, vol. 280 No. 50, Oct. 18, 2005, pp. 41439-41448, XP002391924, ISSN: 0021-9258.

Simon, M.M. et al., "Heat Shock Protein 70 Overexpression Affects the Response to Ultraviolet Light in Murine Fibroblasts," *J Clin Res*, 95(3): 926-933 (1995).

Sobue, G., Molecular Pathogenesis of Motor Neuron Diseases (In Japanese) English abstract, *Nihon Shinkei Seishin Yakurigaku Zasshi*, 21(1): 21-25 (2001).

Stalteri, M.A. et al., "Site-specific conjugation and labelling of prostate antibody 7E11C5.3 (CYT-351) with technetium-99m," *European Journal of Nuclear Medicine* 24(6):651-654, (1997).

Sun et al., Shengwu Huaxue Yu Shengwu Wuli Xuebao, 4(5), 539-550 (1964).

Tanaka, S. et al., "Activiation of T cells recognizing an epitope of heat-shock protein 70 can protect against rat adjuvant arthritis," Journal of Immunology, Nov. 1999, 163(10), 5560-5565.

Tavaria, M. et al., "A Hitchhiker's Guide to the Human Hsp70 Family," *Cell Stress Chaperones*, 1(1): 23-28 (1996).

Todryk, S.M. et al. "Facets of Heat Shock Protein 70 Show Immunotherapeutic Potential,", *Immunology*, 110(1): 1-9 (2003).

Tsuchiya, D. et al., "Overexpression of Rat Heat Shock Protein 70 Reduces Neuronal injury After Transient Focal Ischemia, Transient Global Ischemia, or Kainic Acid-Induced Seizures," *Neurosurgery*, 53(5): 1179-1187 (2003).

Berge et al., "Pharmaceutical Salts," J. Pharm. Sci., 66(1): 1-19, 1977.

Twomey, D., "Anticancer Agents-IX. Derivatives of Pyridine, Pyridazine and Phthalazine," *Proceedings of the Royal Irish Academy*, vol. 74, Sect. B:37-52,(1974).

Biagi, G. et al., "1,5-Diarylsubstituted 1,2,3-triazoles as Potassium Channel Activators. VI," *Il Farmaco*, 59(5): 397-404 (2004), esp. p. 398.

Valeriote, F. et al. "Synergistic Interaction of Anticancer Agents: A Cellular Perspective," *Cancer Chemotherapy Reports*., 59(5): 895-900 (1975).

Vippagunta et al., "Crystalline solids," Advanced Drug Delivery Reviews, 48: 3-26, 2001.

Vleminckx, V. et al., "Upregulation of HSP27 in a Transgenic Model of ALS," *J Neuropathol Exp Neurol*, 61(11): 968-974 (2002).

Voss, R.M. et al., "Gender Differences in the Expression of Heat Shock Proteins: The Effect of Estrogen," *Am J Physiol Heart Circ Physiol*, 285: H687-H692 (2003).

Blondeau, N. et al., "Polyunsaturated Fatty Acids Induce Ischemic and Epileptic Tolerance," *Neuroscience*, 109(2): 231-241 (2002).

Wust, P. et al., "Hyperthermia in Combined Treatment of Cancer," *The Lancet Oncology*, 3(8): 487-497 (Aug. 2002), XP004813895.

Yenari, M.A., "Heat Shock Proteins and Neuroprotection," *Adv Exp Med Biol*, 513: 281-299 (2002).

Yu, Q. et al., "Retinal Uptake of Intravitreally Injected Hsc/Hsp70 and its Effect on Susceptibility to Light Damage," *Molecular Vision*, 7: 48-56 (2001).

Zhang, Y. et al., "Estrogen and Androgen Protection of Human Neurons Against Intracellular Amyloid $\beta_{1-42}$ Toxicity Through Heat Shock Protein 70," *J Neuroscience*, 24(23): 5315-5321 (2004).

Zinner, G. et al., "Über 2-Adamantylhydrazin und einige seiner Vorstufen und Derivate," *Arch. Pharm.* (Weinheim), 317: 1024-1028 (1984).

Gawande, N.G. et al., "Synthesis of Some Thiosemicarbazides and Related Compounds," CAPLUS, 1989, XP002391517.

Wiernik, P.H. et al., "Taxol in Malignant Melanoma," *J. Natl. Cancer Inst. Monogr.*, 15: 185-187 (1993) (abstract only).

* cited by examiner

SYNTHESIS OF TAXOL ENHANCERS

RELATED APPLICATIONS

This application is a continuation of U.S. patent application Ser. No. 11/440,429, filed May 24, 2006, now U.S. Pat. No. 7,435,843, issued Oct. 14 2008, which is a continuation of U.S. patent application Ser. No. 10/807,919, filed Mar. 24, 2004, now U.S. Pat. No. 7,074,952, issued Jul. 11, 2006, which is a continuation of U.S. patent application Ser. No. 10/193,076, filed Jul. 10, 2002, now U.S. Pat. No. 6,825,235, Issued: Nov. 30, 2004, which claims the benefit of U.S. Provisional Application No. 60/304,318, filed Jul. 10, 2001. The entire teachings of these applications are incorporated herein by reference.

BACKGROUND OF THE INVENTION

Many new drugs are now available to be used by oncologists in treating patients with cancer. Often, tumors are more responsive to treatment when anti-cancer drugs are administered in combination to the patient than when the same drugs are administered individually and sequentially. One advantage of this approach is that the anti-cancer agents often act synergistically because the tumors cells are attacked simultaneously with agents having multiple modes of action. Thus, it is often possible to achieve more rapid reductions in tumor size by administering these drugs in combination. Another advantage of combination chemotherapy is that tumors are more likely to be eradicated completely and are less likely to develop resistance to the anti-cancer drugs being used to treat the patient.

One serious limitation of combination chemotherapy is that anti-cancer agents generally have severe side effects, even when administered individually. For example, the well known anti-cancer agent taxol causes neutroperia, neuropathy, mucositis, anemia, thrombocytopenia, bradycardia, diarrhea and nausea. Unfortunately, the toxicity of anti-cancer agents is generally additive when the drugs are administered in combination. As result, certain types of anti-cancer drugs are generally not combined. The combined toxic side-effects of those anti-cancer drugs that are administered simultaneously can place severe limitations on the quantities that can be used in combination. Often, it is not possible to use enough of the combination therapy to achieve the desired synergistic effects. Therefore, there is an urgent need for agents which can enhance the desirable tumor attacking properties of anti-cancer agents without further increasing their undesirable side-effects, and methods for synthesizing such agents.

SUMMARY OF THE INVENTION

It has been reported in the co-pending U.S. Provisional Applications entitled TAXOL ENHANCER COMPOUNDS, filed Jul. 10, 2001, (Application No. 60/304,252), TAXOL ENHANCER COMPOUNDS, filed Mar. 6, 2002 (Application No. 60/361,946) and TAXOL ENHANCER COMPOUNDS, filed Mar. 6, 2002 (Application No. 60/361,936) that certain bis[thio-hydrazide amide] compounds significantly enhance the anti-cancer activity of taxol and analogs of taxol. The entire teachings of these applications are incorporated herein by reference. Disclosed herein are methods of preparing these taxol enhancing compounds.

One embodiment of the present invention is a method of preparing a thiohydrazide product compound from a hydrazide starting compound. The hydrazide starting compound is represented by Structural Formula (I):

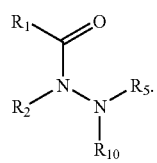

The thiohydrazide product compound is represented by Structural Formula (II):

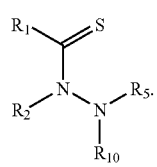

In Structural Formulas (I)-(II), $R_1$ and $R_2$ are independently an aliphatic group, a substituted aliphatic group, an aryl group or a substituted aryl group, or $R_1$ and $R_2$, taken together with the carbon and nitrogen atoms to which they are bonded, form a non-aromatic heterocyclic ring optionally fused to an aromatic ring. When $R_2$ is an aryl group or a substituted aryl group, then $R_5$ is a hydrazine protecting group; and when $R_2$ is an aliphatic or substituted aliphatic group, then $R_5$ is —H or a hydrazine protecting group. $R_{10}$ is —H or a substituted or unsubstituted alkyl group (preferably —H or an unsubstituted alkyl group, more preferably —H or methyl). The method comprises the step of reacting the starting compound with a thionylating reagent.

Another embodiment of the present invention is a method of preparing a product compound represented by Structural Formula (III):

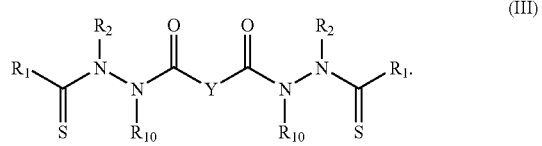

The method comprises the step of reacting Z—C(O)—Y—(CO)—Z or HO—C(O)—Y—(CO)—OH and a carboxylic acid activating agent with the thiohydrazide represented by Structural Formula (II), wherein $R_5$ is —H.

$R_1$, $R_2$ and $R_{10}$ in Structural Formula (III) are as described for Structural Formulas (I)-(II).

Y is a covalent bond or a substituted or unsubstituted straight chained hydrocarbyl group. Preferably, Y is a covalent bond, —C($R_7R_8$)—, —$CH_2CH_2$-, trans-(CH=CH)—, cis-(CH=CH)—, —(CC)— or a 1,4-phenylene group. More preferably, Y is a covalent bond or -C($R_7R_8$)-.

$R_7$ and $R_8$ are each independently —H, an aliphatic or substituted aliphatic group, or $R_7$ is —H and $R_8$ is a substituted or unsubstituted aryl group, or, $R_7$ and $R_8$, taken together, are a C2-C6 substituted or unsubstituted alkylene group.

Each Z is a leaving group.

Another embodiment of the present invention is a method of preparing a product compound represented by Structural Formula (III) from a hydrazide starting compound represented by Structural Formula (I). The hydrazide starting compound is thionylated to form a thiohydrazide represented by Structural Formula (II), as described above. If $R_5$ is —H, then Z—C(O)—Y—(CO)—Z or HO—C(O)—Y—(CO)—OH and a carboxylic acid activating agent is reacted with the thiohydrazide represented by Structural Formula (II) to form the product compound represented by Structural Formula (III), as described above. If $R_5$ is a hydrazine protecting group, the hydrazine protecting group is first removed before reacting with Z—C(O)—Y—(CO)—Z. Z and Y are as described above.

DETAILED DESCRIPTION OF THE INVENTION

The methods disclosed herein can also be used to prepare bis[thio-hydrazide amide] compounds, which, as the term is used herein, refers to a compound represented by Structural Formula (I). In addition, asymmetrical bis[thio-hydrazide amide] compounds can also be prepared by suitable modifications of these procedures. The term "asymmetical bis[thio-hydrazide amide] compound" refers to a compound represented by Structural Formula (IV):

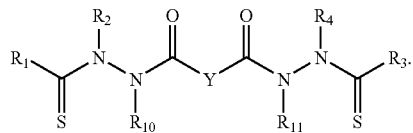

(IV)

$R_1$, $R_2$, $R_7$, $R_8$, $R_{10}$, and Y are as defined above. $R_3$ and $R_4$ are independently an aliphatic group, a substituted aliphatic group, an aryl group or a substituted aryl group, or $R_3$ and $R_4$, taken together with the carbon and nitrogen atoms to which they are bonded, form a non-aromatic heterocyclic ring optionally fused to an aromatic ring. $R_3$ and $R_4$, are independently selected from $R_1$ and $R_2$. $R_{11}$ is —H or a substituted or unsubstituted alkyl group and is selected independently of $R_8$. The method comprises a first step in which a compound represented by HOOC—Y—COOR$_6$ is amidated with a first thiohydrazide starting material represented by Structural Formula (II). $R_6$ is a carboxylic acid protecting group. The amidation forms a first intermediate represented by Structural Formula (V):

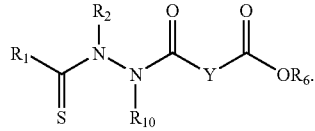

(V)

The protecting group is then removed from the carboxylic acid to form a second intermediate with a free carboxylic acid group. The second intermediate is represented by Structural Formula (VI):

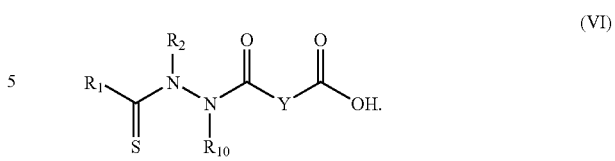

(VI)

The second intermediate is then amidated with a second thiohydrazide starting material represented by Structural Formula (II). The second thiohydrazide starting compound is typically different from the first thiohydrazide starting compound, thereby forming the asymmetical bis[thiohydrazide-amide] represented by Structural Formula (IV).

$R_1$ in Structural Formulas (I)-(VI) can be a substituted or unsubstituted aryl group (preferably a substituted or unsubstituted phenyl group). When $R_1$ in Structural Formulas (I)-(VI) is aryl or substituted aryl, $R_2$ can be a substituted or unsubstituted aliphatic group, preferably a substituted or unsubstituted lower alkyl group (e.g., methyl, ethyl, n-propyl, n-butyl or n-pentyl). Alternatively, when $R_1$ in Structural Formula (I)-(VI) is aryl or substituted aryl, $R_2$ can be a substituted or unsubstituted aryl group, preferably a substituted or unsubstituted phenyl group.

$R_1$ in Structural Formula (I)-(VI) can also be a substituted or unsubstituted aliphatic group, preferably a substituted or unsubstituted lower alkyl group (e.g., methyl, ethyl, n-propyl, n-butyl or n-pentyl). When $R_1$ in Structural Formula (I)-(VI) is a substituted or unsubstituted aliphatic group, $R_2$ can be a substituted or unsubstituted aryl group, preferably a substituted or unsubstituted phenyl group. Alternatively, when $R_1$ in Structural Formula (I)-(VI) is a substituted or unsubstituted aliphatic group, $R_2$ can also be a substituted or unsubstituted aliphatic group, preferably a substituted or unsubstituted lower alkyl group (e.g., methyl, ethyl, n-propyl, n-butyl or n-pentyl).

In another alternative, $R_2$ in Structural Formulas (I)-(VI) is an aliphatic group or a substituted aliphatic group. When $R_2$ in Structural Formulas (I)-(VI) is an aliphatic group or a substituted aliphatic group, $R_1$ is preferably a lower alkyl group or a substituted lower alkyl group.

In yet another alternative, $R_2$ in Structural Formulas (I)-(VI) is an aryl group or a substituted aryl group, more preferably a phenyl group or a substituted phenyl group.

Preferably in Structural Formulas (I)-(VI), $R_1$ is a substituted or unsubstituted aryl group, $R_2$ is methyl or ethyl, $R_7$ is —H and $R_8$ is —H or methyl.

"Thionylating agent" is a reagent which, under suitable, conditions, can convert a ketone, ester or amide into a thioketone, thioester or thioamide, respectively. There are many thionylating agents known to one of ordinary skill in the art. Examples include Lawesson's Reagent, tetraphosphorus pentasulfide, Scheeren's reagent ($P_4S_{10}$-$Na_2S$), $P_4S_{10}$-N (ethyl)$_3$, Davy' Reagent and Heimgarner' reagent. Also known are conditions suitable for carrying out these conversions with thionylating agents. For example, such conditions are disclosed in Fieser and Fieser, "Reagents for Organic Synthesis",Volume 1, John Wiley & Sons, (1975) page 870-71, Fieser and Fieser, "Reagents for Organic Synthesis",Volume 5, John Wiley & Sons, (1975) page 653 and publications cited therein. Suitable conditions are also described in *Bull. Soc. Chim. Belg.* 87:223, 229, 525 (1978), *Synthesis* 1979: 941 (1979), *Tetrahedron* 35:2433 (1979) and *Tetrahedron* 21:4061 (1980). Descriptions of these reagents can also be found in Metzner and Thuillier "Sulfur Reagents in Organic Synthesis", Academic Press, 1994. The relevant portions of these publications are incorporated herein by reference.

Applicants have discovered that thionylating agents can similarly convert hydrazides to the corresponding thiohydrazide. Conditions for thionylating hydrazides are generally the same or similar to those used for thionylating ketones, esters or amides. Although some modification of those conditions may be necessary when reacting hydrazides with thionylating reagents, such modifications can readily be determined by one of ordinary skill in the art. Suitable conditions for preparing thiohydrazides from hydrazides are described in the following paragraphs.

To thionylate hydrazides, typically about one equivalent of the hydrazide is reacted with the thionylating reagent in an inert solvent. In some cases, it may be desirable to use a slight excess of thionylating reagent, for example up to about 1.5 equivalents, preferably no more than about 1.1 equivalents. Suitable inert solvents include ethereal solvents (e.g., diethyl ether, tetrhydrofuran, glyme and 1,4-dioxane), aromatic solvents (e.g., benzene and toluene) or chlorinated solvents (e.g., methylene chloride and 1,2-dichloroethane). The reaction is carried out at temperatures ranging from about room temperature to about 150° C., preferably from about 75° C. to about 125° C. Representative conditions for carrying out these reactions are found in Examples 1-9.

The term "amidating a carboxylic acid" refers to converting a carboxylic acid to an amide or a hydrazide. Many methods for converting a carboxylic acid to an amide are known in the art. Applicants have discovered that these methods can be used to prepare to the bis[thio-hydrazide amide] compounds of the present invention. Typically, the carboxylic acid is first converted into a group that is more readily displaced by an amine or hydrazine than —OH. Thus, —OH is converted into a better leaving group. A "leaving group" is a group which can readily be displaced by a nucleophile.

In one example, —OH of the carboxylic acid is converted into a better leaving group by replacing it with a halogen, typically with chloride. The carboxylic acid is thereby converted into an acid halide, e.g., an acid chloride. Reagents suitable for preparing acid chlorides from carboxylic acids are well known in the art and include thionyl chloride, oxalyl chloride, phosphorus trichloride and phosphorus pentachloride. Typically, each carboxylic acid group is reacted with about one equivalent or a slight excess of thionyl chloride, oxalyl chloride, phosphorus trichloride and phosphorus pentachloride in an inert solvent such as an ethereal solvent (e.g., diethyl ether, tetrahydrofuran or 1,4-dioxane), a halogenated solvent (e.g., methylene chloride or 1,2-dichloroethane) or aromatic solvent (e.g., benzene or toluene). When oxalyl chloride is used, a tertiary amine is often added to accelerate the reaction in quantities ranging from a catalytic amount to about one equivalent relative to oxalyl chloride.

Alternatively, the carboxylic acid is first converted into an "activated ester". An ester —COOR is said to be "activated" when —OR is readily displaced by an amine or hydrazine. —OR is more easily displaced as R becomes more electron withdrawing. Some activated esters are sufficiently stable that they can be isolated, e.g., esters wherein R is phenyl or substituted phenyl. For example, diphenylmalonate can be prepared from malonyl chloride and phenol, both commercially available from Aldrich Chemical Co., Milwaukee, Wis., by procedures described above Other activated esters are more reactive and are generally prepared and used in situ.

Formation of an activated ester in situ requires a "coupling agent", also referred to as a "carboxylic acid activating agent", which is a reagent that replaces the hydroxyl group of a carboxyl acid with a group which is susceptible to nucleophilic displacement. Examples of coupling agents include 1,1-carbonyldiimidazole (CDI), isobutyl chloroformate, dimethylaminopropylethyl-carbodiimide (EDC), dicyclohexyl carbodiimide (DCC). When amidating by in situ generation of an activated ester, an excess of either the carboxylic acid or hydrazine can be used (typically a 50% excess, more typically about a 10-15% excess). However, it is more common when carrying out the present invention to use the hydrazine compound as the limiting reagent. Generally, from about 1.0 equivalent to about 10 equivalents of coupling agent are used relative to each carboxylic acid group, preferably from about 1.0 equivalent to about 1.5 equivalents. When DCC is used, a weak acid such as 1-hydroxybenzotriazole (HOBt) is often added to accelerate the reaction. Typically, about between one to about 1.5 equivalents of HOBt relative to DCC is used, preferably between about one to about 1.2 equivalents. The reaction is generally carried out in inert, aprotic solvents, for example, halogenated solvents such as methylene chloride, dichloroethane and chloroform, ethereal solvents such as tetrahydrofuran, 1,4-dioxane and diethyl ether and dimethylformamide. Suitable reaction temperature generally range from between about 0° to about 100°, but the reaction is preferably carried out at ambient temperature. Representative conditions for carrying out these reactions are found in Examples 1-9.

The compound represented by Structural Formula (V) comprises a carboxylic acid protecting group. Suitable protecting groups for carboxylic acids and conditions for protecting and deprotecting carboxylic acids with these groups are known in the art and are described, for example, in Greene and Wuts, "Protective Groups in Organic Synthesis", John Wiley & Sons (1991). The entire teachings of Greene and Wits are incorporated herein by reference. Specific examples of suitable carboxylic acid protecting groups for Structural Formula (V) include, but are not limited to tert-butoxy, benzoxy, phenoxy, diphenylmethoxy, triphenylmethoxy and methoxymethyl.

The compounds represented by Structural Formulas (I) and (II) can comprise a hydrazine protecting group. Amine protecting groups can also be used for protecting hydrazine groups, and conditions which are suitable for protecting and deprotecting amines with these protecting groups are also suitable for use with hydrazines. Protecting groups for amines and conditions for protecting and deprotecting amines with these protecting groups are known in the art and are disclosed, for example, in Greene and Wuts, "Protective Groups in Organic Synthesis", John Wiley & Sons (1991). Specific examples of suitable hydrazine protecting groups include, but are not limited to, tert-butoxycarbonyl (BOC), benzyloxycarbonyl (CBZ) and fluorenylmethyloxycarbonyl (FMOC).

A "straight chained hydrocarbyl group" is an alkylene group, i.e., -($CH_2$)$_x$-, with one or more (preferably one) methylene groups is optionally replaced with a linkage group. x is a positive integer (e.g., between 1 and about 10), preferably between 1 and about 6, more preferably between 1 and 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine [-N($R^a$)]-, wherein $R^a$ is defined below. A preferred linkage group is -C($R_7R_8$)-, wherein $R_7$ and $R_8$ are defined above. Suitable substitutents for an alkylene group and a hydrocarbaryl group are those which do not substantially interfere with the reactions described herein. $R_7$ and $R_8$ are preferred substituents for an alkylene or hydrocarbyl group.

An aliphatic group is a straight chained, branched or cyclic (non-aromatic hydrocarbon which is completely saturated or which contains one or more units of unsaturation. Typically, a straight chained or branched aliphatic group has from one to about twenty carbon atoms, preferably from one to about ten, and a cyclic aliphatic group has from three to about eight ring carbon atoms. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with three to about eight ring carbon atoms. C1-C20 straight chained and branched alkyl groups and C3-C8 cycloalkyl groups are also referred to herein as "lower alkyl groups".

Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrrolyl, pyrazolyl, pyrazinyl, thiazole, oxazolyl and tetrazole.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl, isoindolyl, 3-isoindolyl.

Non-aromatic heterocyclic rings are non-aromatic carbocyclic rings which include one or more heteroatoms such as nitrogen, oxygen or sulfur in the ring. The ring can be five, six, seven or eight-membered. Examples include tetrahydrofuranyl, tetrahyrothiophenyl, morpholino, thiomorpholino, pyrrolidinyl, piperazinyl, piperidinyl, and thiazolidinyl.

Suitable substituents on a aliphatic, aromatic non-aromatic heterocyclic or benzyl group are those which do not substantially interfere with the reactions described herein. "Interfering with a reaction" refers to substantially decreasing the yield (e.g., a decrease of greater than 50%) or causing a substantial amount of by-product formation (e.g., where by-products represent at least 50% of the theoretical yield). Interfering substituents can be used, provided that they are first converted to a protected form. Suitable protecting groups are known in the art and are disclosed, for example, in Greene and Wuts, "Protective Groups in Organic Synthesis", John Wiley & Sons (1991). Suitable substituents on an aliphatic group, non-aromatic heterocyclic group, benzylic or aryl group (carbocyclic and heteroaryl) include, for example, —OH, halogen (—Br, —Cl, —I and —F), —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SO$_k$R$^a$ (k is 0, 1 or 2) and —NH—C(=NH)—NH$_2$. R$^a$-R$^d$ each are independently an aliphatic, substituted aliphatic, benzyl, substituted benzyl, aromatic or substituted aromatic group, preferably an alkyl, benzylic or aryl group. In addition, —NR$^a$R$^b$, taken together, can also form a substituted or unsubstituted non-aromatic heterocyclic group. A benzylic group, non-aromatic heterocyclic group or aryl group can also have an aliphatic or substituted aliphatic group as a substituent. A substituted alkyl or aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent.

The term "arylene" refers to an aryl group which is connected to the remainder of the molecule by two other bonds. By way of example, the structure of a 1,4-phenylene group is shown below:

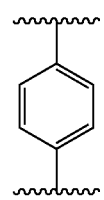

Substituents for an arylene group are as described below for an aryl group.

The present invention is illustrated by the following examples, which are not intended to be limiting in any way.

EXEMPLIFICATION

Example 1

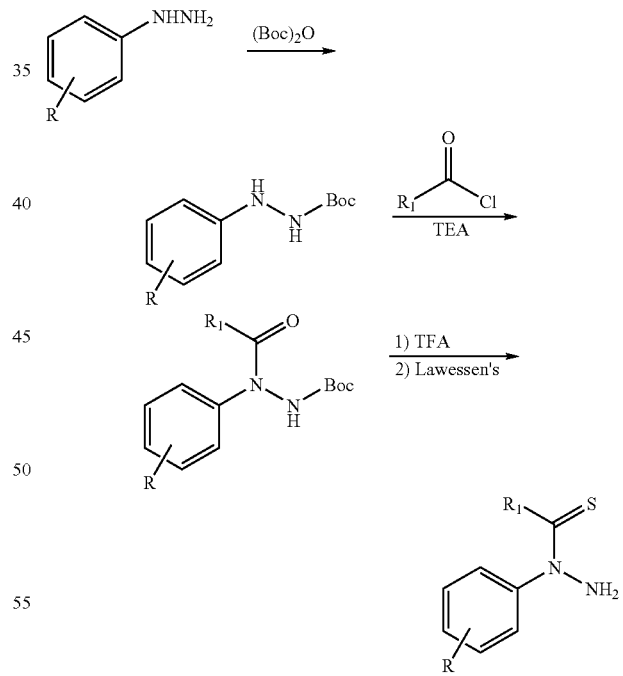

Preparation of Thiocyclohexanoic acid N-phenylhydrazide

Phenyl hydrazine (5.4 g, 50 mmol) was dissolved in dry dichloromethane (50 mL) in a 250 mL round bottom flask. Di-tert-butyl dicarbonate (10.9 g, 50 mmol) was then added with stirring at 0° C. The resultant solution was then stirred under reflux for 3 h. Removal of the volatile components under reduced pressure afforded a colorless solid, which was washed with hexane and dried in vacuo. 10 g (yield 96%) of the product was obtained as a colorless solid, which can be used in the next step without further purification. 2.5 g (12 mmol) of this material was dissolved in dry pyridine (5 mL). Cyclohexanecarbonyl chloride (2.0 ml, 15 mmol) was then added slowly at 0° C. The red solution was stirred at 0° C. for half an hour and the resultant yellow suspension was stirred at room temperature for 3 h before pouring into ice-$H_2O$ (100 mL). The precipitate product was collected by filtration and washed thoroughly with $H_2O$. After one recrystallization from EtOH/$H_2O$, 3.63 g (95%) of N-Phenyl-N-Cyclohexyl-N'-tert-butoxycarbonylhydrazide was obtained as a white powder; mp 141-143° C.; $^1H$ NMR (CDCl$_3$) δ 0.9-2.3 (m, 11H), 1.4 (s, 9H), 6.9 (br, 1H), 7.4 (m, 5H)ppm.

To a solution of N-Phenyl-N-Cyclohexyl-N'-tert-butoxycarbonylhydrazide (1.1 g, 3.46 mmol) in dichloromethane (6 mL) was added trifluoroacetic acid (6 mL) at 0° C. The resultant solution was stirred at 0° C. for half an hour. Volatile components were then removed under reduced pressure to afford a syrup, which was turned into a solid upon standing; this material was briefly mixed with cold 2 N NaOH (5 mL) for a few minutes at 0° C. Solid product was then collected by filtration and recrystallized from hexane to afford cyclohexanoic acid N-phenylhydrazide (0.6 g, 80% yield) as a white powder; $^1H$ NMR (DMSO-d$_6$) δ 0.8-3.2 (m, 1H), 5.3 (s, 2H), 7.0-7.7 (m, 5H); ESMS calcd($C_{13}H_{18}N_2O$): 218.3; found: 241.1 (M+Na)$^+$.

A mixture of cyclohexanoic acid N-phenylhydrazide (0.25 g, 1.15 mmol) and Lawesson's Reagent (0.46 g, 1.15 mmol) in dry toluene (20 mL) was stirred under reflux for 1 h. After being cooled to room temperature, the mixture was filtered through a short column of silica gel (5 g) which was prewashed with benzene. Removal of benzene afforded the crude product as a solid which was purified by column chromatography on silica gel using hexane/EtOAc (4:1 v/v) as eluant. 0.15 g (60%) of thiocyclohexanoic acid N-phenylhydrazide was obtained as an off white solid. $^1H$ NMR (CDCl$_3$) δ 0.8-2.4 (m, 11H), 5.65 (br, 1H), 7.1-7.6 (m, 5H); ESMS calcd ($C_{13}H_{18}N_2S$): 234.1; found: 235.1 (M+H)$^+$.

Example 2

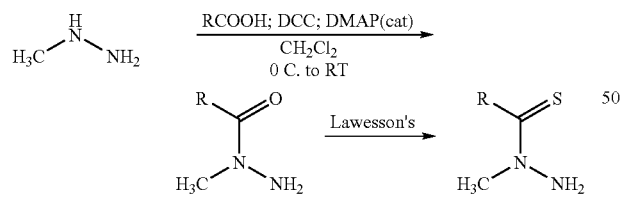

Preparation of 2,5-Dimethoxythiobenzoic acid N-methylhydrazine

DCC (4.5 g, 21.8 mmol) was added in one portion to a solution of 2,5-dimethoxybenzoic acid (3.6g, 20 mol), methylhydrazine (1.2 ml, 23 mmol) and DMAP (30 mg, cat.) in $CH_2Cl_2$(60 ml) cooled in an ice bath. The reaction mixture was stirred overnight at room temperature. The slurry was cooled at −20° C. for 1 h and filtered. The $CH_2Cl_2$ solution was evaporated and the residue was dried in vacuum. The resulting crude product was dissolved in toluene (50 ml). To this solution was added Lawesson's reagent (5.8 g, 14 mmol). The mixture was refluxed for 40 min, cooled to room temperature, and directly subjected to silica gel column chromatography (eluent: 25% to 35% ethyl acetate in hexanes) to give the 2,5-dimethoxythiobenzoic acid N-methylhydrazide (3.7 g, yield: 82%) as off-white solid. $^1H$ NMR (300 MHz, CDCl$_3$): δ 6.88-6.80(m, 3H), 5.46 (s, 2H), 3.84(s, 3H), 3.82 (s, 3H), 3.28(s, 3H).

Example 3

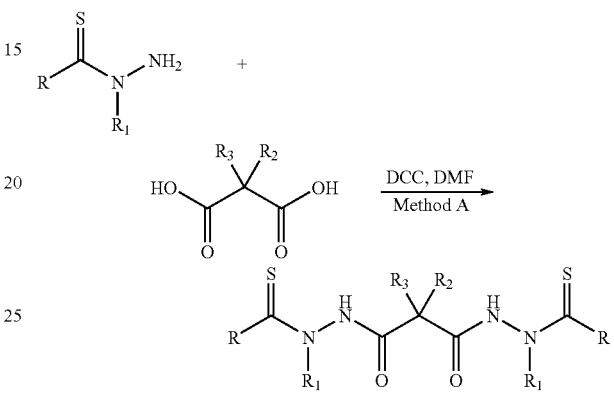

Preparation of N-Malonyl-bis[N'-methyl-N'-(thiobenzoyl)hydrazide]

To a stirred solution of thiobenzoic acid N-methylhydrazide (0.166 g, 10 mmol), HOBt $H_2O$ (0.15 g, 11 mmol) and malonic acid (0.052 g, 5 mmol) in DMF (2 mL) was added DCC (0.22 g, 10.7 mmol) at 0° C. The resultant suspension was stirred at 0° C. for 1 h and at room temperature for 3 h. Precipitated material was filtered off and washed with EtOAc (3×15 mL). Combined filtrate and washings was washed successively with $H_2O$ (2×20 mL), 5% citric acid (20 mL), $H_2O$ (20 mL), Saturated NaHCO$_3$ (20 mL) and brine (20 mL). After being dried over Na$_2$SO$_4$, the solvent was removed under reduced pressure to afford the crude product as a yellow solid, which was washed with warm EtOAc. 0.16 g (yield 80%) of pure product was obtained as a yellow powder. R$_f$ 0.3 (Hexane/EtOAc 1:1 v/v); $^1H$ NMR (CDCl$_3$) δ 3.1-3.8 (m, 6H), 3.4 (s, 2H), 7.1-7.45 (m, 10 H), 9.5-10.5 (m, 1H) ppm; ESMS calcd ($C_{19}H_{20}N_4O_2S_2$): 400.1; found: 399.1 (M−H)$^+$.

Preparation of N-(2-Methylmalonyl-bis{N'-methyl-N'-[(2.5-dimethoxy) thiobenzoyl]hydrazide]:

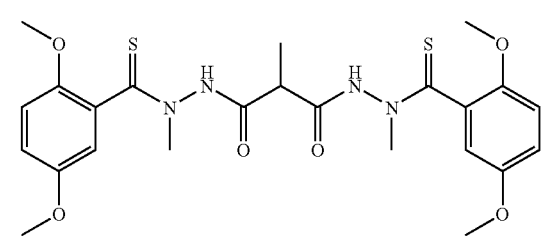

DCC (4 g, 19 mmol) was added to a solution of 2,5-dimethoxythiobenzoic acid N-methylhydrazide (3.7 g, 16.4 mmol) and 2-methylmalonic acid (2 g, 17 mmol) in DMF (20 ml) with stirring at 0° C. The reaction mixture was stirred for 1 h at room temperature. The slurry was cooled at −20° C. for 1 h and filtered. The filtrate was diluted with EtOAc (300 ml), washed with water (50 ml×3), dried with $Na_2SO_4$. The EtOAc solution was concentrated to minimum volume, and subjected to silica gel column chromatography (eluent: 1:4 to 2:1, ethyl acetate: hexanes) to give the title compound (3.5 g, 80%) as yellow powder. $^1$H NMR ($CDCl_3$) δ 10.12-9.14 (2H), 7.12-6.81 (m, 6H), 4.01-3.78(m, 6H), 3.75-3.22(m, 6H), 2.82-2.62(m, 1H), 1.12-0.11(m,3H); ESMS cacld ($C_{24}H_{30}N_4O_6S_2$):534.16; found: 535.1 (M+H).

Preparation of 2-Methylmalonyl-bis(2-Amino-2,3-dihydro-isoindole-1-thione)

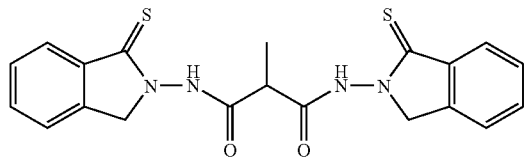

2-carboxybenzaldehyde (150 mg, 1 mmol) and carbazic acid (132 mg, 1 mmol) in 40 ml methanol was stirred at room temperature for 4 h. To this solution was added Pd/C (60 mg, containing 50% $H_2O$), the reaction was under $H_2$ atmosphere for 3 h. The reaction mixture was filtered, and the solvent was evaporated. The resulting residue was subjected to silica gel column chromatography (eluent: 20% to 50%, EtOAc in hexanes) to yield 50 mg of product. $^1$H NMR (300 MHz, $CDCl_3$): 8.71-7.45 (m, 4H), 4.78 (s, 2H), 1.61(s, 9H). The resulting product was dissolved in $CF_3COOH$ (5 ml), stirred for 30 min. The $CF_3COOH$ was evaporated, and the residue was subjected to silica gel column chromatography (eluent: 50% to 0%, hexanes in EtOAc) to give 2-amino-2,3-dihydro-isoindol-1-one (26 mg) as a white solid. $^1$H NMR (300 MHz, $CDCl_3$): 7.85-7.39 (m, 4H), 4.54 (s, 2H). MS: 149 (M+H). Subsequent Lawesson's thiolation and DCC coupling with 2-methylmaloic acid under conditions described above afforded 2-methylmalonyl-bis(2-amino-2,3-dihydro-isoindole-1-thione) as a yellow powder. $^1$HNMR ($CDCl_3$) δ 10.35 (s, 2H), 8.21-7.51(m, 8H), 5.15(s, 4H), 1.62 (s, 3H); ESMS cacld ($C_{20}H_{18}N_4O_2S_2$): 410.09; found: 411.1 (M+H).

Example 4

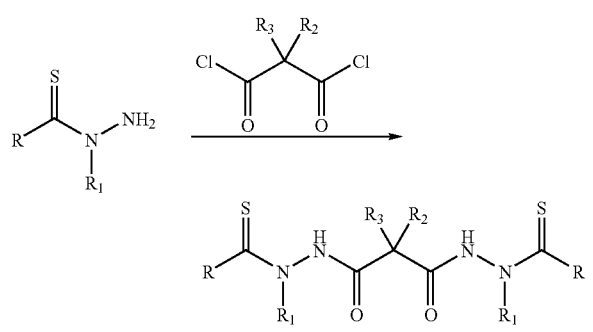

Preparation of N-Malonyl-bis[N'-methyl-N'-(thiobenzoyl)hydrazide]

To a solution of thiobenzoic acid N-methylhydrazine (10 g) stirred at 0 C. were added subsequently triethylamine (8.5 mL) and malonyl dichloride (3.05 mL). The reaction mixture was stirred for 10 min, washed with water (3×50 mL), dried over sodium sulfate and concentrated. Purification by recrystallization from methylene dichloride (35 mL) gave the product as light yellow crystals (9.0 g, 75%).

Example 5

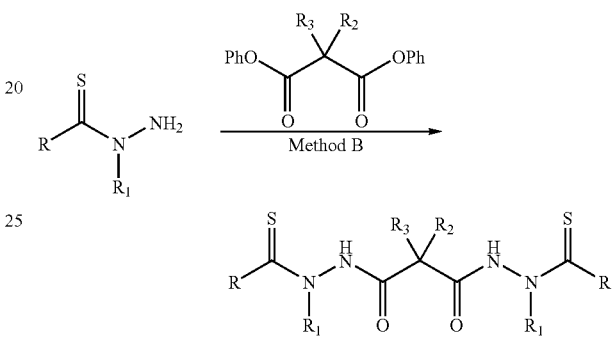

Preparation of N-Malonyl-bis[N'-methyl-N'-(thiobenzoyl)hydrazide]

A stirred solution of thiobenzoic acid N-methylhydrazide (1.66 g, 10 mmol) and diphenyl malonate (1.30 g, 5.08 mmol) in dry THF (100 mL) was heated to reflux for 72 h. Volatile components were then removed under reduced pressure. The crude product was purified by column chromatography on silica gel using a mixture of hexane and EtOAc as eluant (gradient from 4:1 v/v to 1:1 v/v). 1.07 g (51% yield) of pure product N-malonyl-bis[N'-methyl-N'-(thiobenzoyl)hydrazide] was obtained as a yellow powder. The physical properties of this compound was identical to the same product by obtained by the synthetic route described above.

Example 6

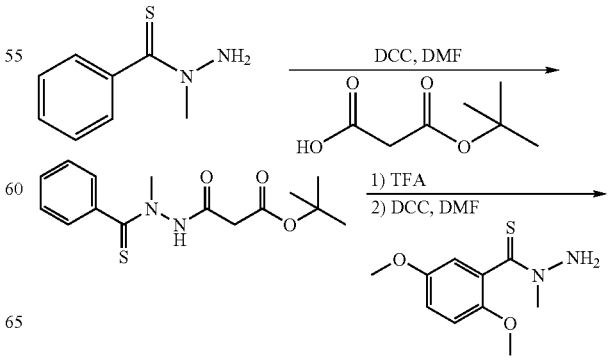

-continued

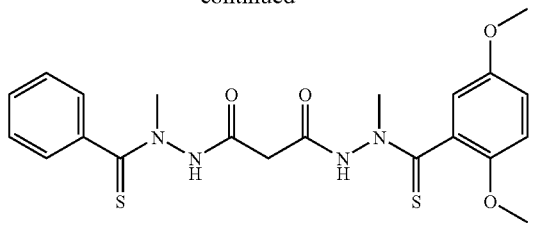

A slurry of thiobenzoic acid N-methylhydrazide (1.0 g, 6 mmol), mono-tert-butyl malonate (1.0 mL, 6 mmol), HOBtH$_2$O (0.98 g, 7.2 mmol), and DCC (1.34 g, 6.5 mmol) in DMF (5 mL) was stirred at 0° C. for 3 h and then at room temperature for 3h. Precipitated material was filtered off and washed with EtOAc (3×20 mL). Combined filtrate and washings was washed successively with H$_2$O (2×20 mL), 5% citric acid (20 mL), H$_2$O (20 mL), saturated NaHCO$_3$ (20 mL) and brine (20 mL). After being dried over Na$_2$SO$_4$, the solvent was removed under reduced pressure to afford the crude product as a solid, which was washed with Et$_2$O. 0.94 g (yield 51%) of pure product N'-methyl-N'-thiobenzoyl-hydrazinocarbonyl)-acetic acid tert-butyl ester was obtained as a yellow powder. $^1$H NMR (CDCl$_3$) δ 1.6-1.7 (ds, 9H), 3.1-4.1 (m, 5 H), 7.3-7.7 (m, 5H), 9.7-10.3 (ds, 1H)ppm; ESMS calcd (C$_{15}$H$_{20}$N$_2$O$_3$S): 308; found: 307 (M−H)$^+$.

A solution of N'-Methyl-N'-thiobenzoyl-hydrazinocarbonyl)-acetic acid tert-butyl ester (0.19g, 0.6 mmol) and TFA (0.12 mL, 1.6 mmol) in dry DCM (10 mL) was stirred at 10° C.-15° C. for 12 h (reaction was monitored by TLC). Volatile components were removed under reduced pressure (bath temperature below 5° C.). After being dried in vacuo, DMF (3 mL) was added followed by the addition of DCC (0.13 g, 0.6 mmol), HOBT H$_2$O (93 mg, 0.7 mmol) and Thio-2,5-dimethoxybenzoic acid N-methylhydrazide (0.13 g, 0.57 mmol). The resultant solution was stirred at 0° C. for half an hour and then at room temperature for 3h. Precipitated material was filtered off and washed with EtOAc (3×10 mL). Combined filtrate and washings was washed successively with H$_2$O (2×10 mL), 5% citric acid (10 mL), H$_2$O (10 mL), Saturated NaHCO$_3$ (20 mL) and brine (20 mL). After being dried over Na$_2$SO$_4$, the solvent was removed under reduced pressure to afford the crude product as an oil, which was purified by SGC (4:1 hexane/EA to 2:1 EtOAc/Hexane). 0.14 g (yield 53%) of pure product was obtained as a yellow powder. $^1$H NMR (CDCl$_3$) δ 3.1-3.9 (m, 18H), 6.7-7.4 (m, 9H) ppm; ESMS calcd (C$_{21}$H$_{24}$N$_4$O$_4$S2): 460.1; found: 461.1 (M+H)$^+$.

Example 7

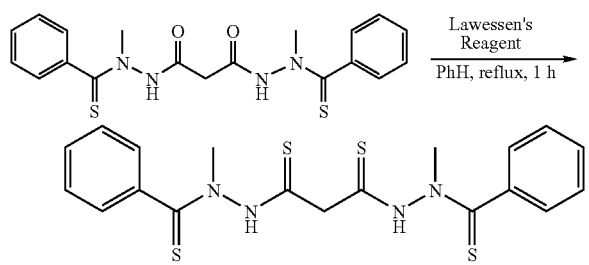

A stirred mixture of N-malonyl-bis-[N'-phenyl-N'-(thioacetyl)hydrazide] (0.1 g, 0.25 mmol) and Lawesson's reagent (0.15 g, 0.37 mmol) in dry benzene (20 mL) was heated to reflux for 1 h. After being cooled to room temperature, the mixture was filtered through a layer of silica gel, washed with THF (2×15 mL). The filtrate and washings were combined and concentrated under reduced pressure. Flush column chromatography on silica gel (hexane to 4:1 hexane/EtOAc to 2:1 hexane/EtOAc) afforded N-bisthiomalonyl-bis[N'-phenyl-N'-thioacetyl)hydrazide) as a clear syrup (16 mg, 15%). $^1$H NMR (CDCl$_3$) δ 3.80-3.95 (m, 8H), 7.02-7.30 9 m, 10H). ESMS calcd (C$_{19}$H$_{20}$N$_4$S$_4$): 432.06; found: 433.0 (M+H)$^+$.

Example 8

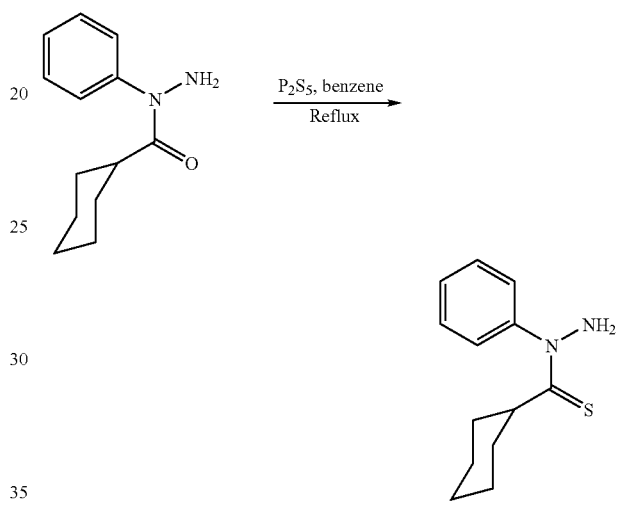

To a stirred solution of Cyclohexanoic acid N-phenylhydrazide (0.1 g, 0.45 mmol) in dry benzene (5 mL) was added P$_2$S$_5$ (0.2 g, 0.45 mol). The resultant suspension was heated to reflux for 3 h. After being cooled to room temperature, the mixture was diluted with benzene (5 mL) and was filtered through a short column of silica gel (2 g), washed with benzene and 2:1 hexane/EtOAc (15 mL each). The filtrate and washings were combined and concentrated to afford a solid. Crystallized from hexane to provide the intermediate thiocyclohexanoic acid N-phenylhydrazide as an off white solid; $^1$H NMR (CDCl$_3$) δ 0.8-2.4 (m, 11H), 5.65 (br, 1H), 7.1-7.6 (m, 5H); ESMS calcd (C$_{13}$H$_{18}$N$_2$S): 234.1; found: 235.1 (M+H)$^+$.

Example 9

The compounds shown below were prepared by the procedures described above. Analytical data is provided for these compounds.

$^1$H NMR (CDCl$_3$) δ 3.1-3.8 (m, 6H), 3.4 (s, 2H), 7.1-7.45 (m, 10H), 9.5-10.5 (m, 1H) ppm; ESMS calcd (C$_{19}$H$_{20}$N$_4$O$_2$S$_2$): 400.1; found: 399.1 (M−H)$^+$.

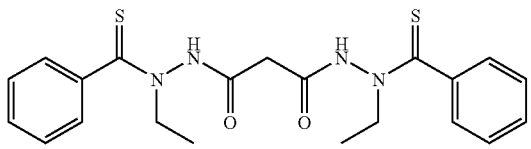

¹H NMR (CDCl₃) δ 1.0-1.35 (m, 6H), 3.0-4.3 (m, 6H), 7.05-7.40 (m, 10H), 9.1-10.1 (m, 2H); ESMS cacld (C₂₁H₂₄N₄O₂S₂): 428.8; found: 427 (M−H)⁺. Anal Calc For C₂₁H₂₄N₄O₂S₂ (428.13) C, 58.85; H, 5.64; N, 13.07; S, 14.96. Found: C, 58.73; H, 5.62; N, 12.97; S, 14.96.

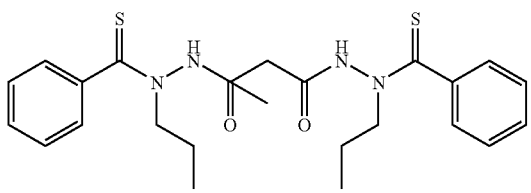

¹H NMR (CDCl₃) δ 0.7-1.0 (m, 6H), 1.4-1.9 (m, 4H), 3.1-4.2 (m, 6H), 7.1-7.4 (m, 10H), 8.9-10.2 (m, 2H) ppm; ESMS (C₂₃H₂₈N₄O₂S₂): 456.1; found: 455.1 (M−H)⁺.

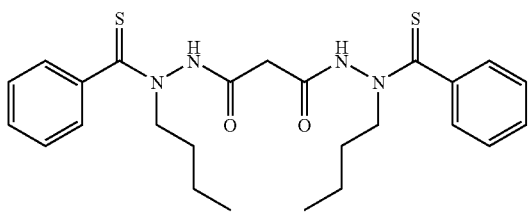

mp 141-143° C.; ¹H NMR (CDCl₃) δ 0.6-1.05 (m, 6H), 1.1-1.9 (m, 8H), 3.0-4.2 (m, 6H), 7.0-7.35 (m, 10H), 8.9-11 (ms, 2H). ESMS (C₂₅H₃₂N₄O₂S₂): 484.2; found: 483.1 (M−H)⁺. Anal Calc For C₂₅H₃₂N₄O₂S₂ (484.2) C, 61.95; H, 6.65; N, 11.56; S, 13.23. Found: C, 61.98; H, 6.52; N, 11.26; S, 13.16.

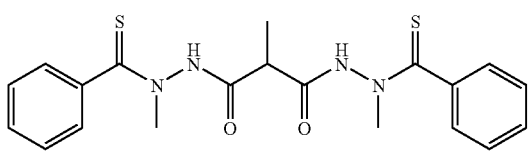

²H NMR (DMSO-d₆) δ 0.4-0.9 (dd, 3H, J=7), 2.7 (q, 1H), 3.1-3.6 (m, 6H), 7.1-7.5 (m, 10H), 10.9 (br, 2H)ppm; ESMS (C₂₀H₂₂N₄O₂S₂): 414; found: 413 (M−H)⁺.

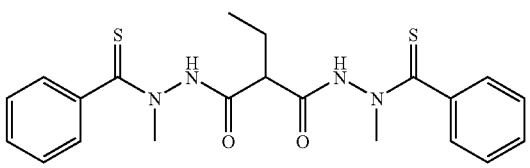

¹H NMR (CDCl₃) δ 0.5 (t, 3H, J=7), 1.1-1.6 (m, 2H), 2.7 (t, 1H, J=7), 3.1-3.3 (m, 6H), 7.0-7.3 (m, 10H), 10.25 (s, 2H) ppm; MS (C₂₁H₂₄N₄O₂S₂): 428.1; found: 427.1 (M−H)⁺.

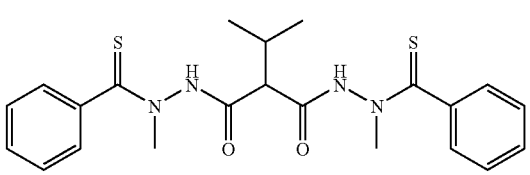

¹H NMR (CDCl₃) δ 0.5 (d, 6H, J=7), 0.9-1.2 (m, 1H), 3.0-41 (m, 7H), 7.1-7.4(m, 10H), 10.3 (s, 2H)ppm; ESMS (C₂₂H₂₆N₄O₂S₂): 442.1; found: 441.1 (M−H)⁺.

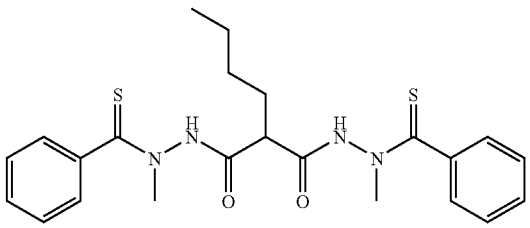

¹H NMR (CDCl₃) δ 0.4-1.3 (m, 5H), 1.5-1.8 (m, 2H), 3.0-3.7 (m, 6H), 7.1-7.5 (m, 10H), 11 (s, 2H)ppm; MS (C₂₃H₂₈N₄O₂S₂): 456.1; found: 455.1 (M−H)³⁰.

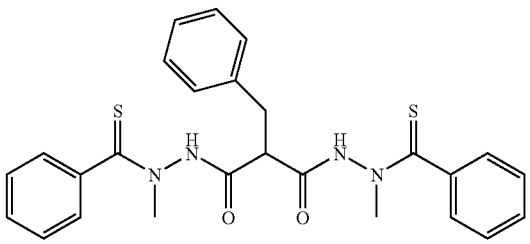

¹H NMR (CDCl₃) δ 2.1 (d, 2H, J=7), 2.9 (t, 1H, J=7), 3.1-3.5 (m, 6H), 6.8-7.4 (m, 15 H), 11 (s, 2H)ppm; MS (C₂₆H₂₆N₄O₂S₂): 490.1; found: 489.1 (M−H)⁺.

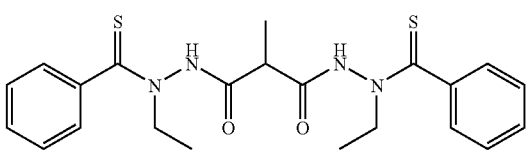

¹H NMR (CDCl₃) δ 0.4 (d, 3H, J=7), 1.0-1.4 (m, 6H), 2.75 (q, 1H), 3.0-4.3 (m, 4H), 7.1-7.4 (m, 10H), 10.6 (s, 2H); ESMS Calc For (C₂₂H₂₆N₄O₂S₂): 442.1; found: 441.1 (M−H)⁺; Anal Calc For C₂₂H₂₆N₄O₂S₂ (442.15) C, 59.70; H, 5.92; N, 12.66; S, 14.49. Found: C, 59.64; H, 5.92; N, 12.59; S, 14.47.

¹H NMR (CDCl₃) δ 0.4 (d, 3H, J=7), 2.7 (q, 1H, J=7), 3.0-3.8 (m, 6H), 7.2-8.2 (m, 8H), 10.5-10.7 (ms, 2H) ppm; ESMS calcd (C₂₀H₂₀Cl₂N₄O₂S₂): 482.0; found: 481.0 (M−H)⁺.

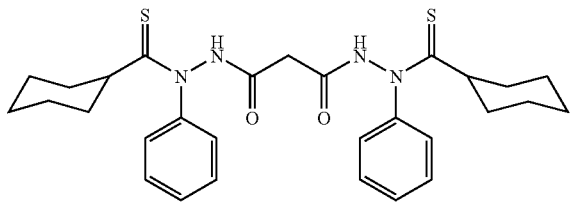

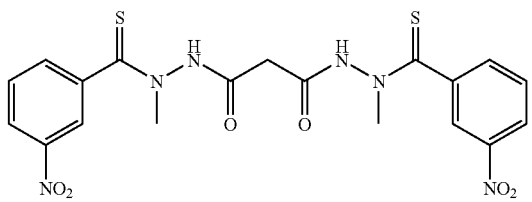

¹H NMR (DMSO-d₆) δ 0.9-1.8m, 22H), 3.1-3.5 (m, 2H), 7.2-7.6 (m, 10H), 11.1-11.7 (ms, 2H) ppm; ESMS calcd (C₂₉H₃₆N₄O₂S₂):536.3; found: 537.3(M−H)⁺.

¹H NMR (CDCl₃) δ 2.9-3.8 (m, 6H), 7.3-7.7 (m, 4H), 8.0-8.3 (m, 4H), 10.9 (s, 2H); ESMS calcd (C₁₀H₁₈N₆O₆S₂): 490.0; found: 489.0 (M−H)⁺.

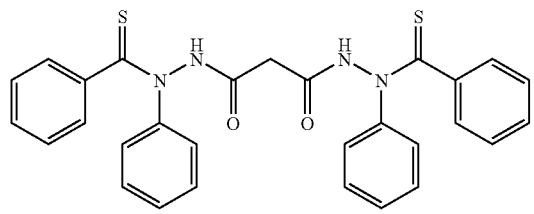

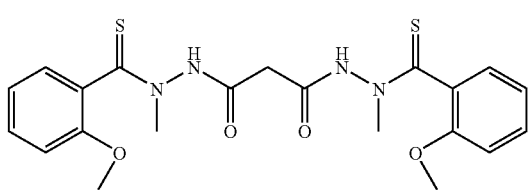

¹H NMR (DMSO-d₆) δ 3.20 (br, 2H), 7.1-7.6 (m, 20H), 11.5 (s, 2H)ppm; ESMS calcd (C29H24N4O2S2): 524.1; found: 523.1 (M−H)⁺.

¹H NMR (CDCl₃) δ 3.1-3.9 (m, 14H), 6.7-7.8 (m, 8H), 9.0-10 (m, 2H) ppm; ESMS calcd (C₂₁H₂₄N₄O₄S₂): 460.1; found: 459.1 (M−H)⁺.

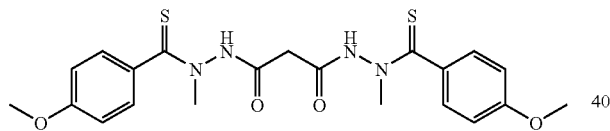

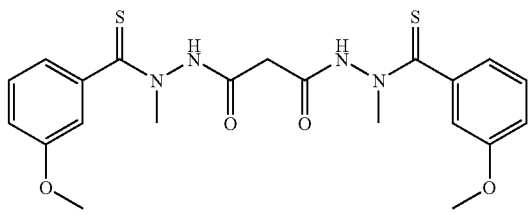

¹H NMR (CDCl₃) δ 3.0-4.3 (m, 14H), 6.6-7.5 (m, 8H), 10.4 (s, 2H) ppm; ESMS calcd (C₂₁H₂₄N₄O₂S₂): 460.2; found: 461.2 (M+H)⁺.

(SBR-11-5032): ¹H NMR (CDCl₃) δ 3.0-3.9 (m, 14H), 6.7-7.3 (m, 8H), 9.0-10 (m, 2H) ppm; ESMS calcd (C₂₁H₂₄N₄O₄S₂): 460.1; found: 459.1 (M−H)⁺.

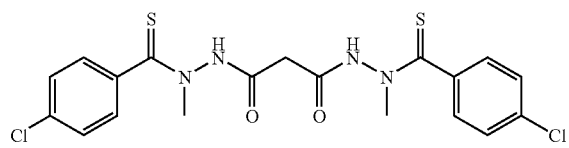

¹H NMR (CDCl₃) δ 2.65-3.60 (m, 8H), 7.2-7.4 (m, 8H), 11.1 (br, 2H); ESMS calcd (C₁₉H₁₈Cl₂N₄O₂S₂): 468.0; found: 467.9 (M−H)⁺.

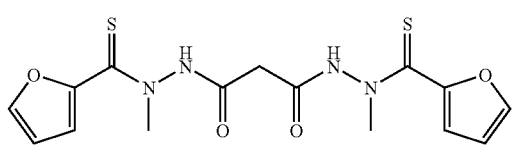

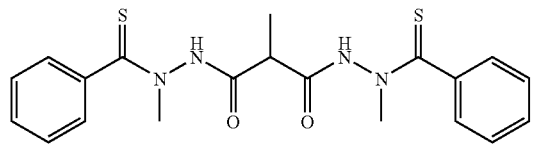

¹H NMR (acetone-d₆)δ 3.5 (s, 2H), 6.45 (d, 2H, J=5), 6.9 (d, 2H, J=5), 7.2-7.6 (m, 12H), 10.6 (s, 2H) ppm; ESMS calcd (C₂₅H₂₀N₄O₄S₂): 504.1; found: 503.1 (M−H)⁺.

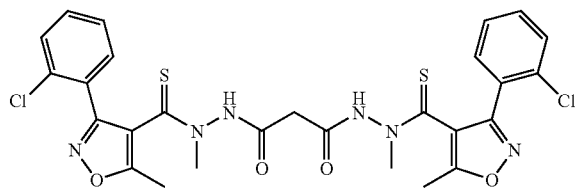

¹H NMR (DMSO-d6) δ 2.60 (s, 6H), 3.05 (s, 6H), 3.40 (s, 2H), 7.15-7.50 (m, 8H)ppm; ESMS calcd (C₂₇H₂₄Cl₂N₆O₄S₂): 630.1; found: 629.1 (M–H)⁺.

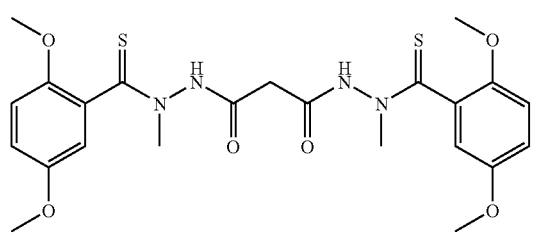

¹H NMR (CDCl₃) δ 10.06-8.82 (2H), 7.16-6.81(m, 6H), 4.01-3.81(m, 6H), 3.78-3.11(m, 6H), 2.81-2.58(m, 2H): ESMS cacld (C₂₃H₂₈N₄O₆S₂): 520.15; found: 521 (M+H).

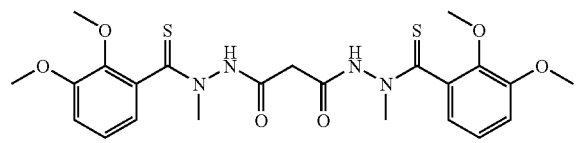

¹H NMR (CDCl₃) δ 10.38-9.01 (2H), 7.12-6.82 (m, 6H), 3.92-3.78(m, 12H), 3.75-3.06(m, 6H), 2.61-2.51 (m, 2H); ESMS cacld (C₂₃H₂₈N₄O₆S₂): 520.15; found: 521 (M+H).

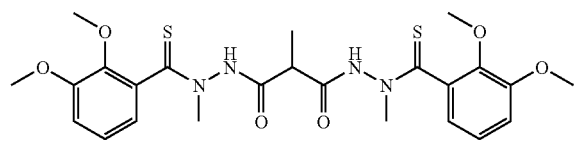

¹H NMR (CDCl₃) δ 9.45-8.63 (2H), 7.18-6.81 (m, 6H), 4.01-3.80(m, 6H), 3.78-3.24(m, 6H), 2.62-2.50(m, 1H), 1.74-0.11 (m, 3H); ESMS cacld (C₂₄H₃₀N₄O₆S₂): 534.16; found: 535 (M+H).

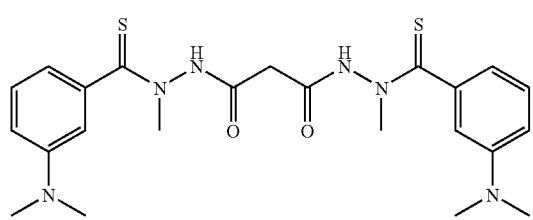

¹H NMR (CDCl₃) δ 10.19-8.61 (2H), 7.26-6.52(m, 6H), 3.81-3.08(m, 8H), 3.01-2.88(m, 12H). ESMS cacld (C₂₃H₃₀N₆O₂S₂): 486.19; found: 487 (M+H).

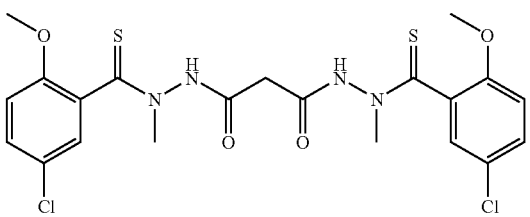

¹H NMR(CDCl₃) δ 9.92-8.80 (2H), 7.41-6.72 (m, 6H), 4.01-3.81(m, 6H), 3.80-3.15 (m, 6H), 2.76-2.42(m, 2H); ESMS cacld (C₂₁H₂₂Cl₂N₄O₄S₂):528.05; found: 529(M+H).

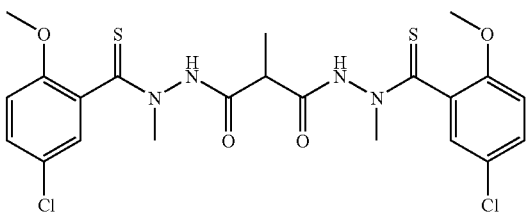

¹H NMR (CDCl₃) δ 10.21-9.02(2H), 7.60-6.81 (m, 6H), 4.14-3.88(m, 6H), 3.87-3.18 (m,6H), 2.84-2.65(m, 1H),1.10-0.16 (m, 3H); ESMS cacld (C₂₂H₂₄Cl₂N₄O₄S₂): 542.06; found: 543(M+H).

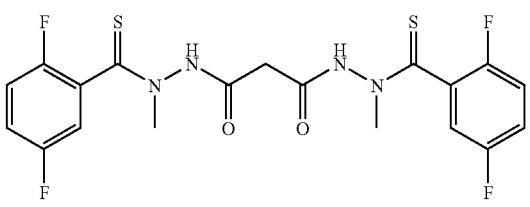

¹H NMR (CDCl₃) δ 10.02-9.20 (2H), 7.63-7.01 (m, 6H), 4.21-3.22(m, 6H), 1.88-1.36 (m, 2H); ESMS cacld (C₁₉H₁₆F₄N₄O₂S₂): 472.07; found: 473 (M+H).

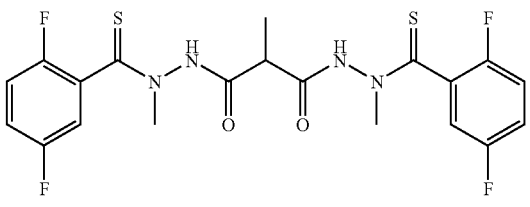

¹H NMR (CDCl₃) δ 7.93-7.61 (2H), 7.40-6.92 (m, 6H), 3.98-3.41 (m, 6H), 2.19-0.93 (m, 4H); ESMS cacld (C₂₀H₁₈F₄N₄O₂S₂): 486.08; found: 487 (M+H).

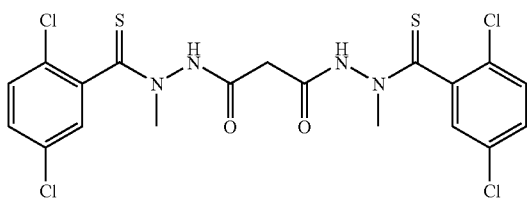

¹H NMR(CDCl₃) δ 10.12-9.21(2H), 7.67-7.23 (m, 6H), 3.94-3.22 (m, 6H), 2.01-1.21 (m, 2H); ESMS cacld (C₁₉H₁₆Cl₄N₄O₂S₂): 535.95; found: 537(M+H).

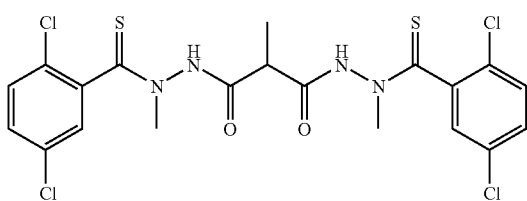

¹H NMR (CDCl₃) δ 7.78-7.23 (2H), 4.56-3.10 (m, 6H), 2.34-1.12 (m, 4H); ESMS cacld (C₂₀H₁₈Cl₄N₄O₂S₂): 549.96; found: 551 (M+H).

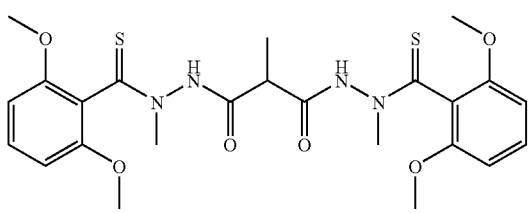

¹H NMR (CDCl₃) δ 9.92-9.01 (2H), 7.38-7.15 (m, 3H), 6.66-6.51 (m, 3H), 3.98-3.75 (m, 12H), 3.72-3.21(m, 6H), 2.01-0.42 (m, 4H); ESMS cacld (C₂₄H₃₀N₄O₆S₂): 534.16; found: 535 (M+H).

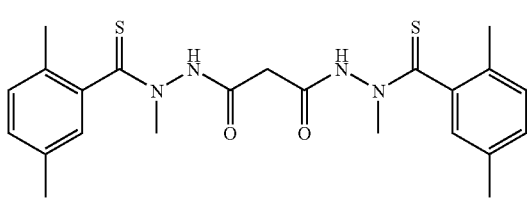

¹H NMR (CDCl₃) δ 10.51-9.82 (2H), 7.42-6.80 (m, 6H), 3.92-3.04(m, 6H), 2.60-1.21 (m, 14H); ESMS cacld (C₂₃H₂₈N₄O₂S₂): 456.17; found: 457(M+H).

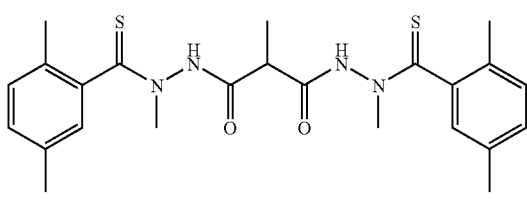

¹H NMR (CDCl₃) δ 10.51-8.82 (2H), 7.11-6.89 (m, 6H), 3.81-3.02 (m, 6H), 2.40-1.02 (m, 16H); ESMS cacld (C₂₄H₃₀N₄O₂S₂): 470.18; found: 471(M+H).

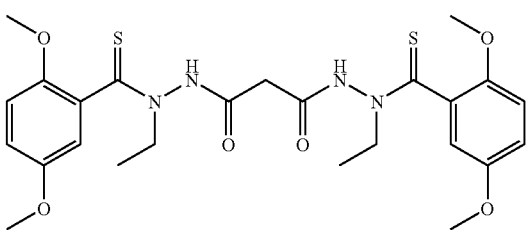

¹H NMR (CDCl₃) δ 9.86-8.42 (2H), 7.01-6.6 (m, 6H), 4.18-3.51 (m, 16H), 3.22-2.26 (2H), 1.40-1.04 (m, 6H); ESMS cacld (C₂₅H₃₂N₄O₆S₂):548.18; found: 547 (M−H).

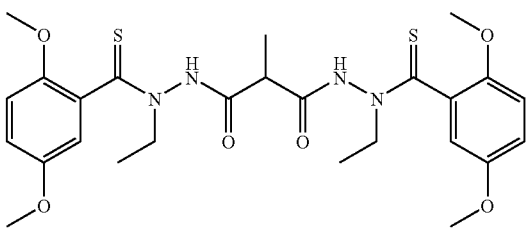

¹H NMR (CDCl₃) δ 9.99-8.41 (2H), 7.01-6.68 (m, 6H), 4.18-3.56 (m, 16H), 1.40-0.02 (m, 10H); ESMS cacld (C₂₆H₃₄N₄O₆S₂): 562.19; found: 561(M−H).

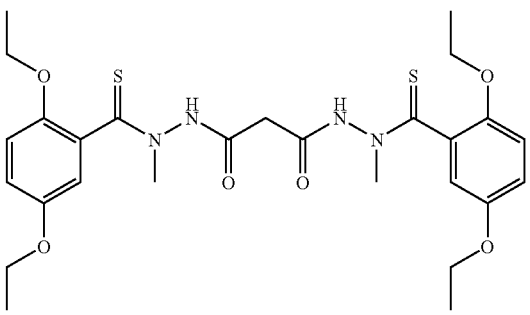

¹H NMR (CDCl₃) δ 10.12-8.82 (2H), 7.03-6.62 (m, 6H), 4.21-3.87 (m, 8H), 3.84-3.01(m, 6H), 2.71-2.42 (m, 2H), 1.56-1.21 (m, 12H); ESMS cacld (C₂₇H₃₆N₄O₆S₂): 576.21; found: 577(M+H).

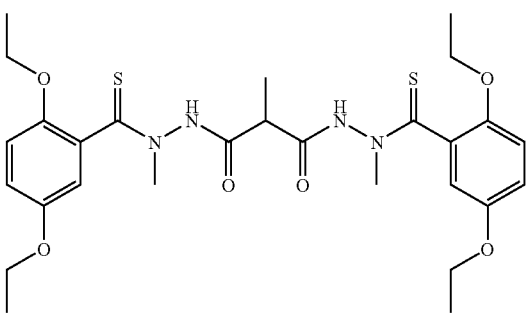

¹H NMR (CDCl₃) δ 9.81-8.79 (2H), 7.01-6.64 (m, 6H), 4.21-3.81(m, 8H), 3.80-3.22 (m, 6H), 1.54-1.20 (m, 13H), 1.01-0.16 (m, 3H); ESMS cacld (C$_{28}$H$_{38}$N$_4$O$_6$S$_2$): 590.22; found: 591 (M+H).

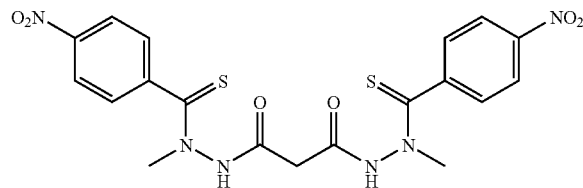

¹H NMR (DMSO-d₆): δ 8.25 (d, J=8.1 Hz, 4H), 7.50 (d, J=8.1 Hz, 4H), 3.7-3.3 (m, 8H); ESMS cacld for C$_{19}$H$_{18}$N$_6$O$_6$S$_2$: 490.1; Found: 489.0 (M−H).

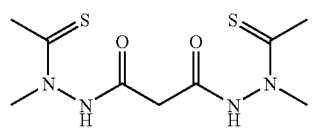

¹H NMR (CDCl₃): δ 3.6-3.4 (m, 8H), 2.7-2.5 (m, 6H); ESMS cacld for C$_9$H$_{16}$N$_4$O$_2$S$_2$: 276.1; Found: 274.9 (M−−H).

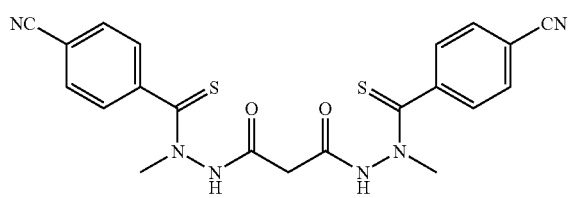

¹H NMR (CDCl₃): δ 10.25 (m, 2H), 7.7-7.4 (m, 8H), 3.7 (m, 2H), 3.35 (m, 6H); ESMS cacld for C$_{21}$H$_{18}$N$_6$O$_2$S$_2$: 450.1; Found: 449.0 (M−H).

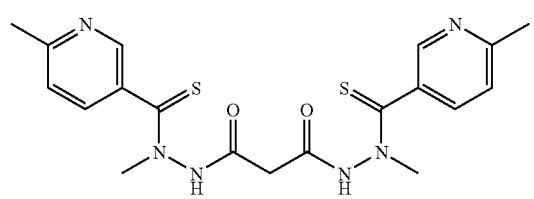

¹H NMR (CDCl₃): δ 8.2 (s, 2H), 7.7-7.5 (m, 4H), 3.7-3.4 (m, 8H), 2.9-2.8 (m, 6H); ESMS cacld for C$_{19}$H$_{22}$N$_6$O$_2$S$_2$: 430.1; Found: 431.1 (M+H).

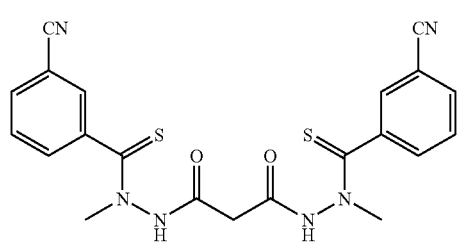

¹H NMR (CDCl₃): δ 10.0-9.2 (m, 2H), 7.9-7.45 (m, 8H), 4.0-3.4 (m, 8H); ESMS cacld for C$_{21}$H$_{18}$N$_6$O$_2$S$_2$: 450.1; Found: 451.0 (M+H).

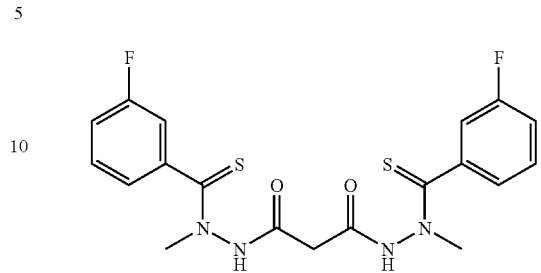

¹H NMR (CDCl₃): δ 10.1-9.4 (2H), 7.5-7.2 (m, 8H), 3.9-3.3 (m, 8H); ESMS cacld for C$_{19}$H$_{18}$F$_2$N$_4$O$_2$S$_2$: 436.1; Found: 437.1 (M+H).

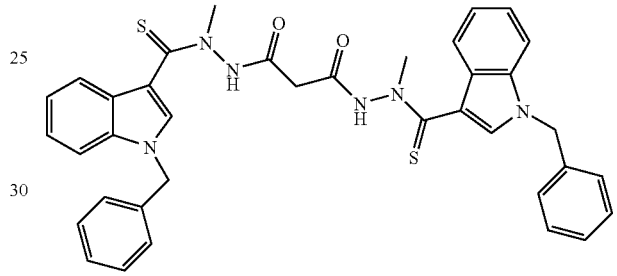

¹H NMR (CDCl₃): δ 3.3 (s, 2H), 3.6 (s, 6H), 5.25 (s, 4H), 7.05-7.3 (m, 16H), 7.6 (s, 2H), 7.9 (d, 2H, J=6), 10.56 (s, 2H)ppm; ESMS calcd (C$_{37}$H$_{34}$N$_6$O$_2$S$_2$): 658.2; found: 659.2 (M+H)⁺.

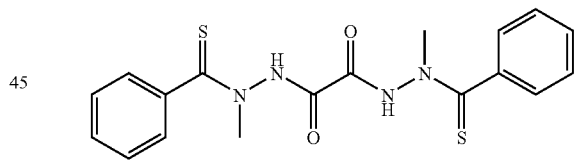

¹H NMR (DMSO) δ 11.98 (2H), 7.44-7.12 (m, 10H), 3.69-3.14(s, 6H). ESMS cacld (C$_{18}$H$_{18}$N$_4$O$_2$S$_2$): 386.09: found: 387.1 (M+H).

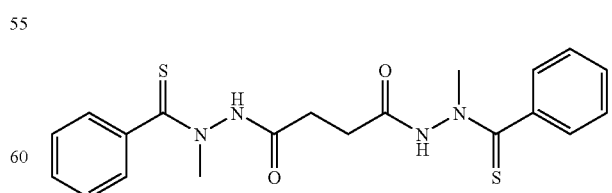

¹H NMR (CHCl₃) δ 9.48-8.55 (2H), 7.56-7.20(m, 10H), 3.80-3.31(m, 6H), 2.88-2.22(m, 4H). ESMS cacld (C$_{20}$H$_{22}$N$_4$O$_2$S$_2$): 414.12; found: 415.1 (M+H).

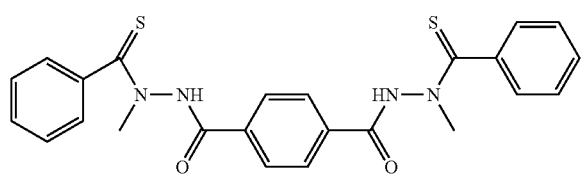

¹H NMR (300 MHz, CDCl₃) δ 10.21-9.91 (m, 2H), 8.06-7.32 (m, 14H), 3.91-3.56 (m, 6H). ESMS cacld (C₂₄H₂₂N₄O₂S₂): 462.12; found: 463 (M+H).

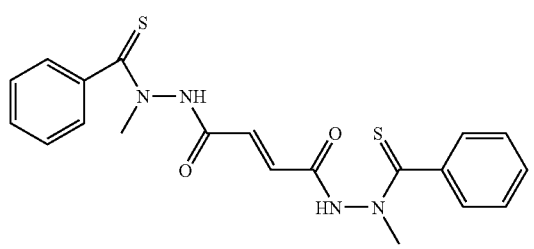

¹H NMR (300 MHz, DMSO-d₆) δ 11.60-11.40 (m, 2H), 7.48-6.46(m, 12H), 3.64-3.3.30(m, 6H). ESMS cacld (C₂₀H₂₀N₄O₂S₂): 412.10; found: 413 (M+H).

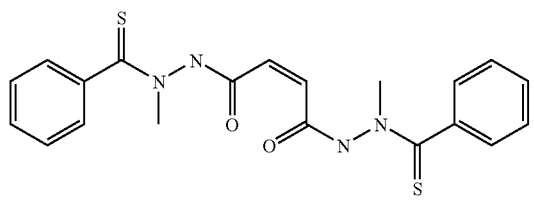

¹H NMR (300 MHz, CDCl₃) δ 7.58-7.20(m, 12H), 3.68-3.20 (m, 6H). ESMS cacld (C₂₀H₂₀N₄O₂S₂): 412.10; found: 413 (M+H).

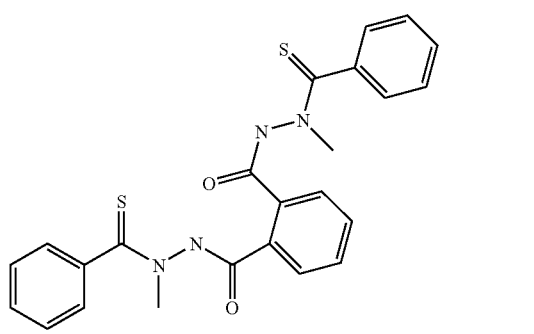

¹H NMR (300 MHz, CDCl₃) δ 9.65-8.70 (2H), 8.01-7.21(m, 14H), 3.84-3.40(m, 6H). ESMS cacld (C₂₄H₂₂N₄O₂S₂): 462.12: found: 463 (M+H).

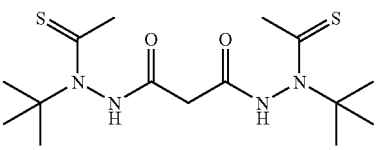

¹H NMR (CDCl₃): δ 2.63 (s, 2H); 2.18 (s, 6H); 1.25 (s, 18H). MS calcd for C₁₅H₂₈N₄O₂S₂: 360.2; Found: 383.1 (M+Na).

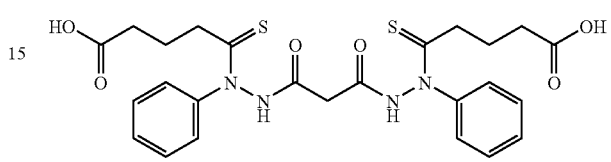

¹H NMR (CDCl₃): δ 7.3 (m, 10H); 3.2 (m, 2H); 2.45 (t, J=7.4 Hz, 4H); 2.21 (t, J=7.4 Hz, 4H); 1.90 (m, 8H). MS calcd for C₂₅H₂₈N₄O₆S₂: 544.15; Found: 567.2 (M+Na).

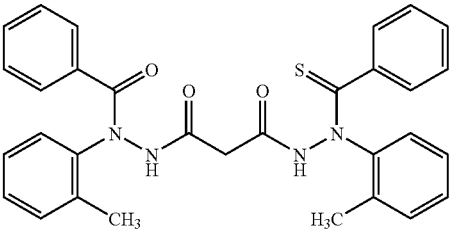

¹H NMR (CDCl₃): δ 7.4-1 (m, 18H); 3.3 (br s, 2H); 2.5 (br s, 6H). MS calcd for C₃₁H₂₈N₄O₃S: 536.2: Found: 537.2 (M+H).

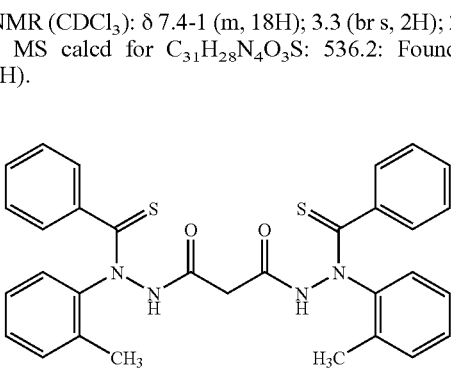

¹H NMR (CDCl₃): δ 7.2 (m, 18H); 3.5 (br s, 2H); 2.4 (br s, 6H). MS calcd for C₃₁H₂₈N₄O₂S₂: 552.2: Found: 553.2 (M+H).

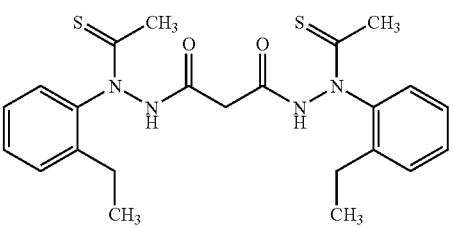

¹H NMR (CDCl₃): δ 7.8-7.4 (br s, 8H), 3.75-3.5 (m, 2H), 3.95-3.8 (m, 4H), 2.58 (s, 6H), 1.4 (m, 6H). ESMS cacld for C₂₃H₂₈N₄O₂S₂: 456.2; Found: 479.2 (M+Na).

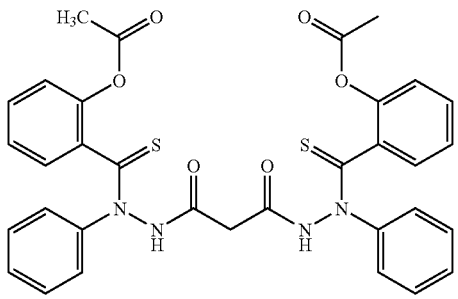

¹H NMR (CDCl₃): δ 7.5 (br s, 18H), 3.4 (br s, 2H), 2.45 (s, 6H). ESMS cacld for C₃₃H₂₈N₄O₆S₂: 640.1; Found 641.1 (M+H).

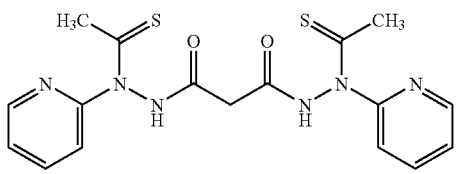

¹H NMR (CDCl₃): δ 8.3-8.05 (m, 4H), 7.75 (t, J=8.0 Hz, 2H), 7.1 (br s, 2H), 3.74 (s, 2H), 2.38 (s, 6H). ESMS cacld for C₁₇H₁₈N₆O₂S₂: 402.1. Found: 403.1 (M+H).

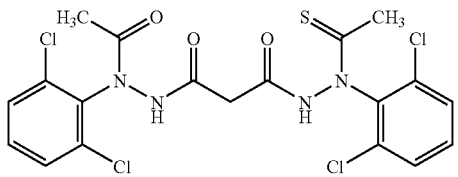

¹H NMR (CDCl₃): δ 7.7-7.2 (m, 6H), 3.2 (s, 2H), 2.58 (s, 3H), 2.15 (s, 3H). ESMS cacld for C₁₉H₁₆Cl₄N₄O₃S: 519.9; Found: 520.9 (M+H).

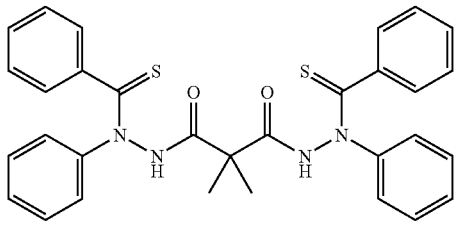

¹H NMR (CDCl₃-D₂O): δ 7.45-7.15 (m, 20H), 1.6 (br s, 6H). ESMS cacld for C₃₁H₂₈N₄O₂S₂: 552.2; Found: 553.2 (M+H).

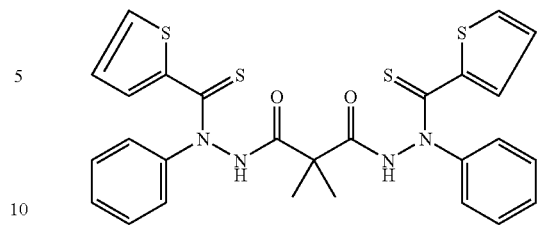

¹H NMR (DMSO-d₆): δ 11.3 (s, 2H), 7.75 (d, J=6.0 Hz, 2H), 7.5-7.4 (m, 12H); 6.9 (m, 2H); ESMS cacld for C₂₇H₂₄N₄O₂S₄: 564.1; Found: 565.2 (M+H).

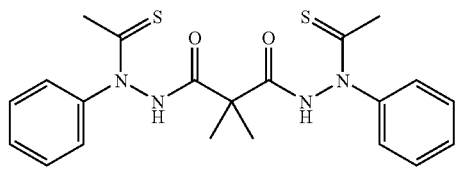

¹H NMR (CDCl₃): δ 7.38 (m, 10H), 2.40 (s, 6H), 1.5-1.6 (6H); ESMS cacld for C₂₁H₂₄N₄O₂S₂: 564.1; Found: 565.2 (M+H).

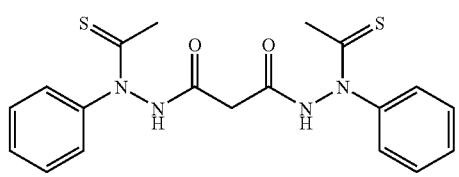

¹H NMR (DMSO-d6): δ 11.5 (m, 2H); 7.5 (m, 10H); 3.2 (m, 2H); 2.6 (s, 3H); 2.5 (s, 3H). MS calcd (400.1); Found: 423.1 (M+Na).

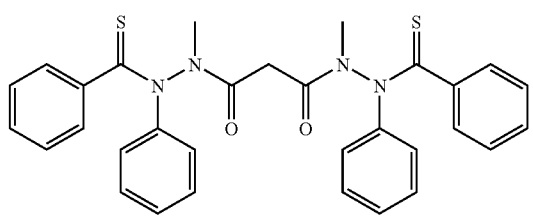

¹H NMR (CDCl₃) δ 3.3-4.5 (m, 8H), 7.1-7.8 (m, 20H)ppm; ESMS calcd (C₃₁H₂₈N₄O₂S₂): 552; found: 551 (M–H)⁺.

While this invention has been particularly shown and described with references to preferred embodiments thereof, it will be understood by those skilled in the art that various changes in form and details may be made therein without departing from the scope of the invention encompassed by the appended claims.

What is claimed is:
1. A method of preparing a compound represented by the following structural formula:

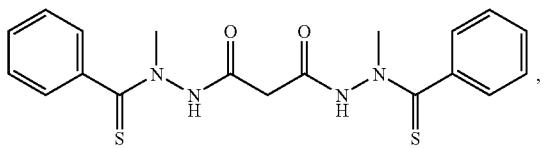, said method comprising the step of reacting Z-C(O)—CH$_2$—C(O)-Z or HO—C(O)—CH$_2$—(CO)—OH and a carboxylic acid activating agent with a thiohydrazide compound represented by the following structural formula:

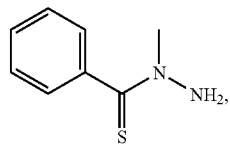

wherein each Z is a leaving group.

2. The method of claim 1, wherein the method comprises the step of reacting Z-C(O)—CH$_2$—C(O)-Z with the thiohydrazide compound, and both Zs are —Cl or —OR, wherein R is phenyl or phenyl substituted with an electron-withdrawing group.

3. The method of claim 1, wherein the method comprises the step of reacting HO—C(O)—CH$_2$—C(O)—OH and a carboxylic acid activating agent with the thiohydrazide compound.

4. The method of claim 3, wherein the carboxylic acid activating agent is selected from the group consisting of 1,1'-carbonyldiimidazole (CDI), isobutyl chloroformate, dimethylaminopropylethyl-carbodiimide (EDC), and dicyclohexyl carbodiimide (DCC).

5. The method of claim 4, wherein the carboxylic acid activating agent is dicyclohexyl carbodiimide (DCC).

6. The method of claim 1, wherein the thiohydrazide compound is prepared by reacting a compound represented by the following structural formula:

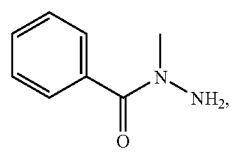

with a thionylating agent.

7. The method of claim 6, wherein the thionylating agent is selected from the group consisting of Lawesson's Reagent, phosphorus pentasulfide, Scheeren's Reagent (P$_4$S$_{10}$-Na$_2$S), P$_4$S$_{10}$-N(ethyl)$_3$, Davy's Reagent and Heimgarner's reagent.

8. The method of claim 7, wherein the thionylating agent is Lawesson's Reagent.

* * * * *